(12) United States Patent
Zwierstra et al.

(10) Patent No.: US 12,079,034 B2
(45) Date of Patent: Sep. 3, 2024

(54) BRAIN SIGNAL SENSING HEADSET

(71) Applicant: Neurolutions, Inc., Santa Cruz, CA (US)

(72) Inventors: Jan Zwierstra, Glendale, CA (US); Eric Claude Leuthardt, St. Louis, MO (US); Kern Bhugra, Santa Cruz, CA (US); Timothy Proulx, Santa Cruz, CA (US)

(73) Assignee: Neurolutions, Inc., Van Nuys, CA (US)

( * ) Notice: Subject to any disclaimer, the term of this patent is extended or adjusted under 35 U.S.C. 154(b) by 0 days.

(21) Appl. No.: 18/583,641

(22) Filed: Feb. 21, 2024

(65) Prior Publication Data

US 2024/0201737 A1    Jun. 20, 2024

Related U.S. Application Data

(63) Continuation of application No. PCT/IB2022/057909, filed on Aug. 24, 2022.

(60) Provisional application No. 63/260,363, filed on Aug. 27, 2021.

(51) Int. Cl.
*G06F 3/01* (2006.01)
*G06F 1/16* (2006.01)

(52) U.S. Cl.
CPC ............ *G06F 1/163* (2013.01); *G06F 1/1656* (2013.01); *G06F 3/015* (2013.01)

(58) Field of Classification Search
CPC . A61B 5/24–291; A61B 5/6803; A61B 5/369; A61B 5/4064; G06F 1/163; G06F 1/1656; G06F 3/015; G06F 3/011
See application file for complete search history.

(56) References Cited

U.S. PATENT DOCUMENTS

| 2012/0143020 A1* | 6/2012 | Bordoley | A61B 5/291 |
| | | | 600/383 |
| 2017/0123495 A1 | 5/2017 | Leuthardt et al. | |
| 2017/0143228 A1* | 5/2017 | Leuthardt, Jr. | G06F 3/011 |
| 2018/0153470 A1* | 6/2018 | Gunasekar | A61B 5/6803 |

(Continued)

FOREIGN PATENT DOCUMENTS

| CN | 109480836 A | 3/2019 |
| JP | 2019076713 B | 2/2023 |
| KR | 20180137756 A | 12/2018 |

OTHER PUBLICATIONS

International Search Report and Written Opinion dated Nov. 29, 2022 for PCT Patent Application No. PCT/IB2022/057909.

*Primary Examiner* — Temesghen Ghebretinsae
*Assistant Examiner* — Ivelisse Martinez Quiles
(74) *Attorney, Agent, or Firm* — MLO, a professional corp.

(57) ABSTRACT

Devices for recording brain activity of a subject include a first arm shaped to extend along a subject's head, the first arm having a first aperture that allows access to the subject's head. A sensor assembly of the device has multi-directional adjustability in orientation. The sensor assembly includes a shell configured for multi-directional rotation; a sleeve inside the shell; an elastic element attaching a first end of the sleeve to an interior end of the shell; and a sensor removably inserted into the sleeve, with a contact surface of the sensor facing the subject's head. The device also includes a housing that contains an energy source and operational components for the sensor assembly.

24 Claims, 19 Drawing Sheets

(56) References Cited

U.S. PATENT DOCUMENTS

2018/0220968 A1* 8/2018 Funane ................ A61B 5/6803
2021/0369535 A1   12/2021 Ishimine et al.
2021/0393955 A1* 12/2021 Hagedorn .............. A61B 5/291

* cited by examiner

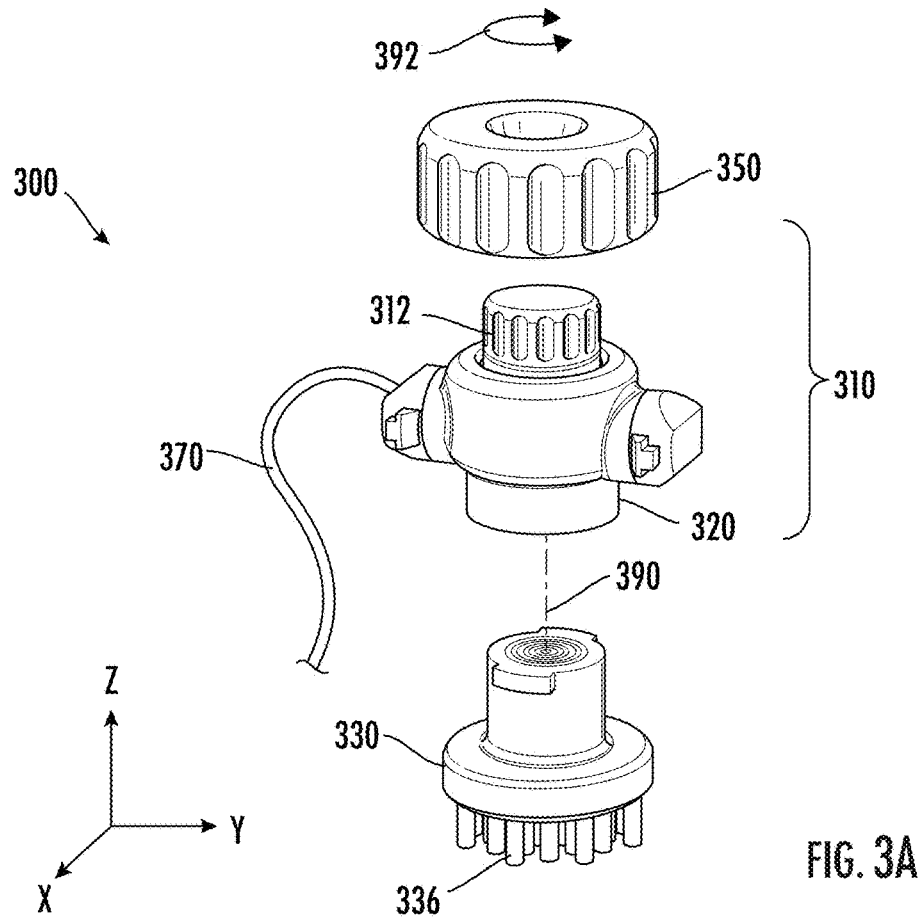
FIG. 3A
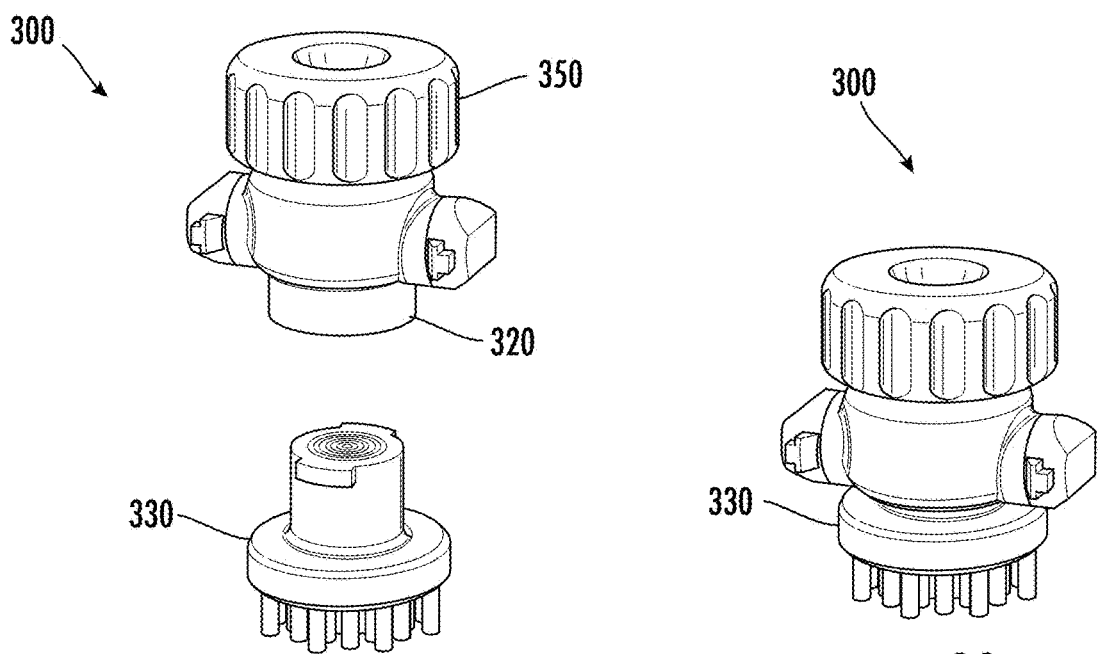
FIG. 3B
FIG. 3C

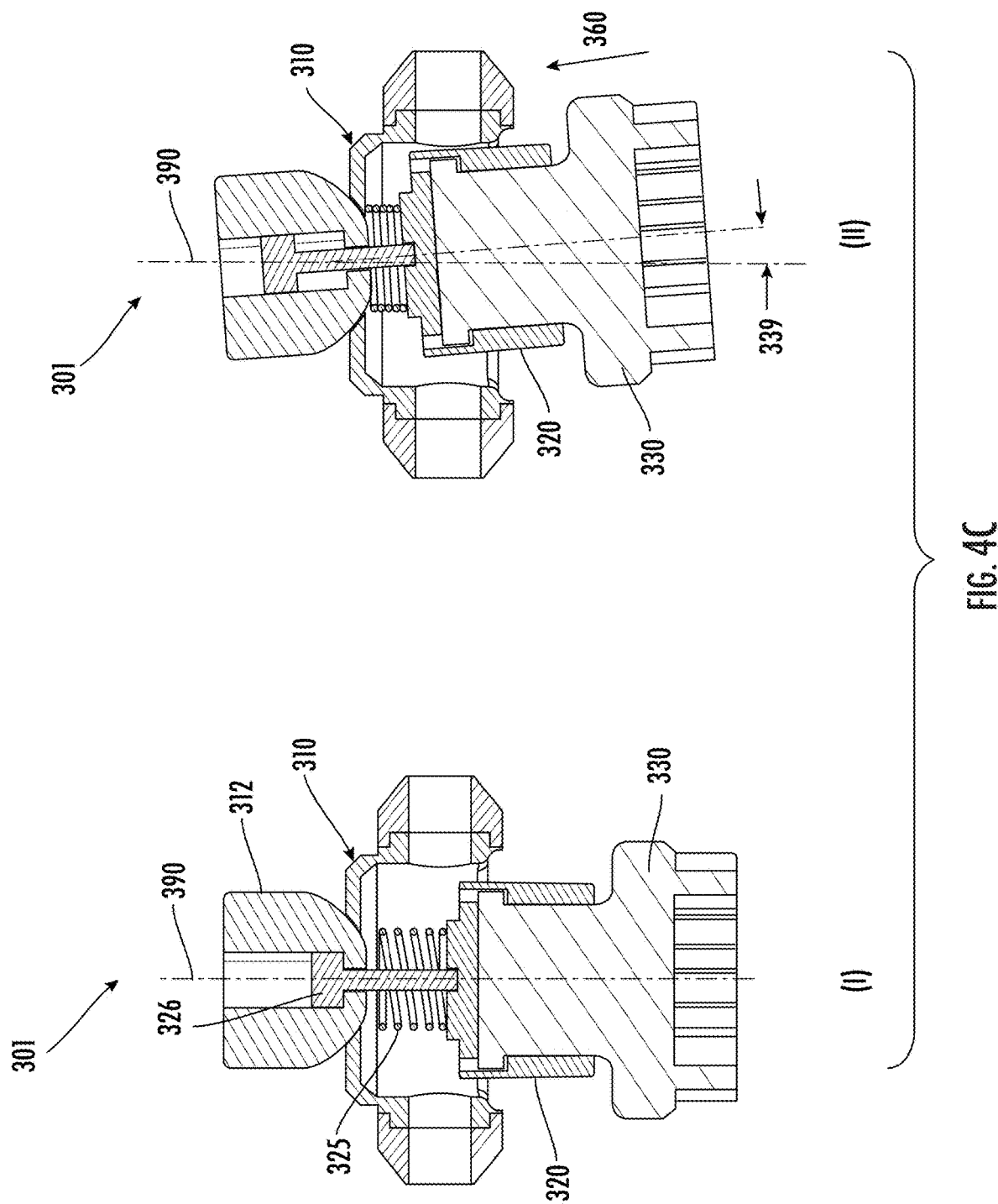

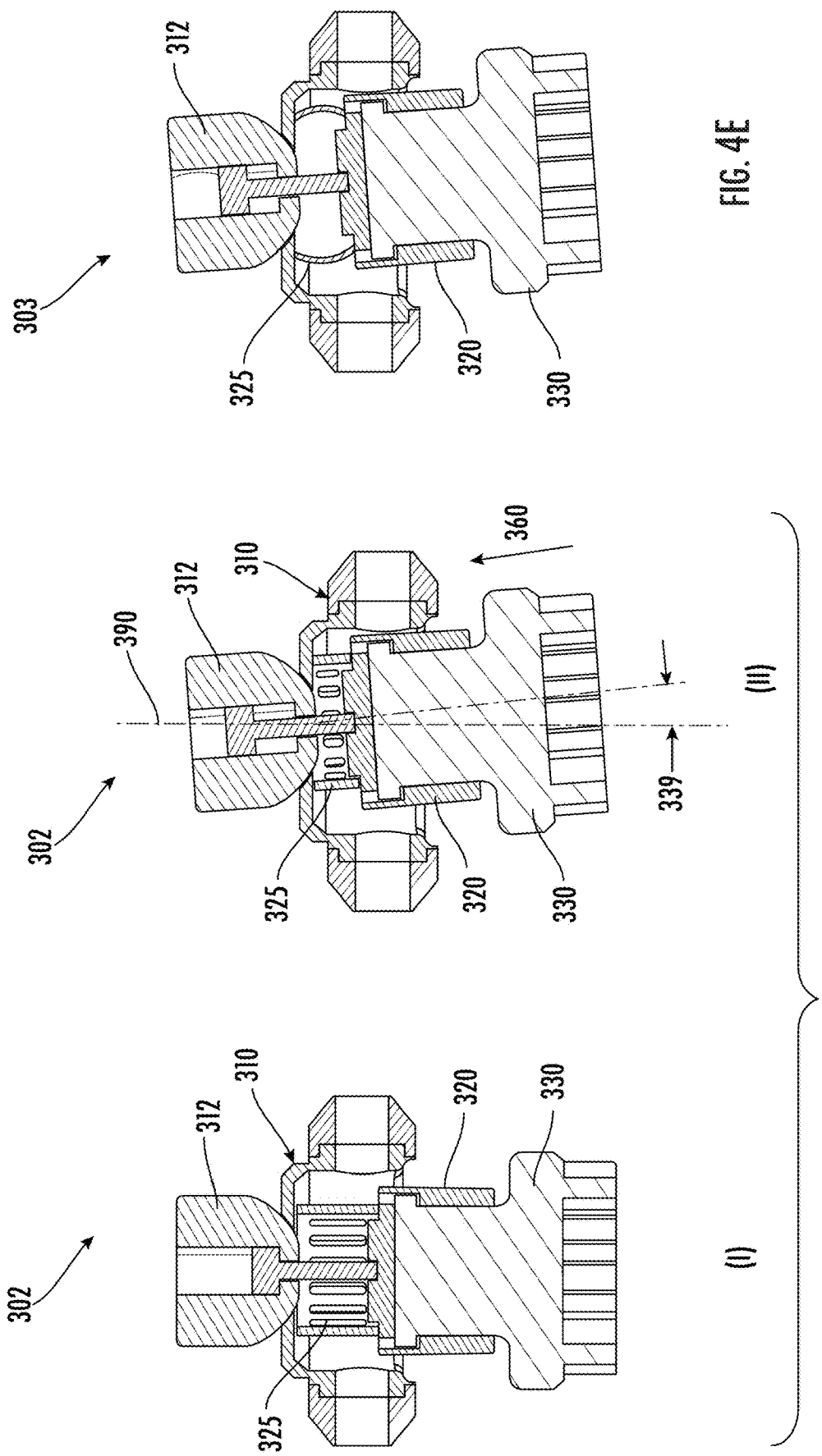

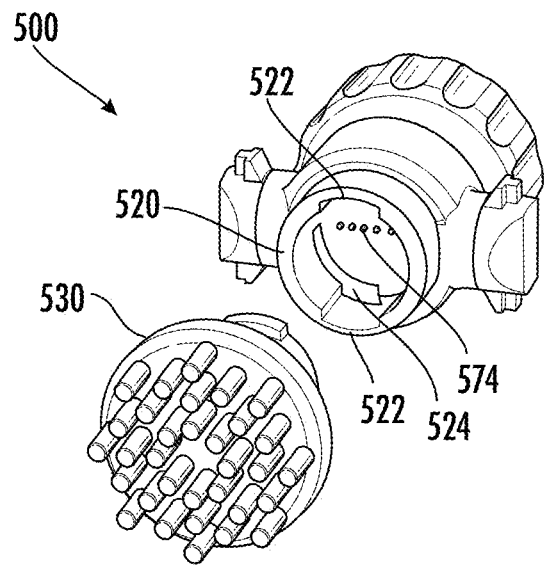
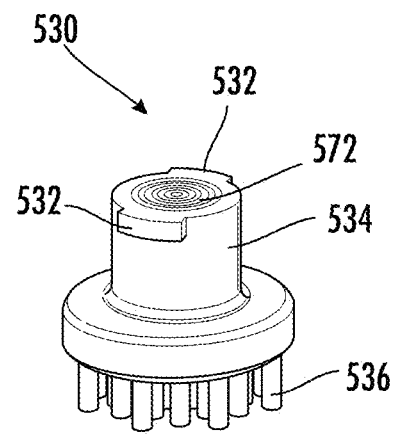
FIG. 5A            FIG. 5B
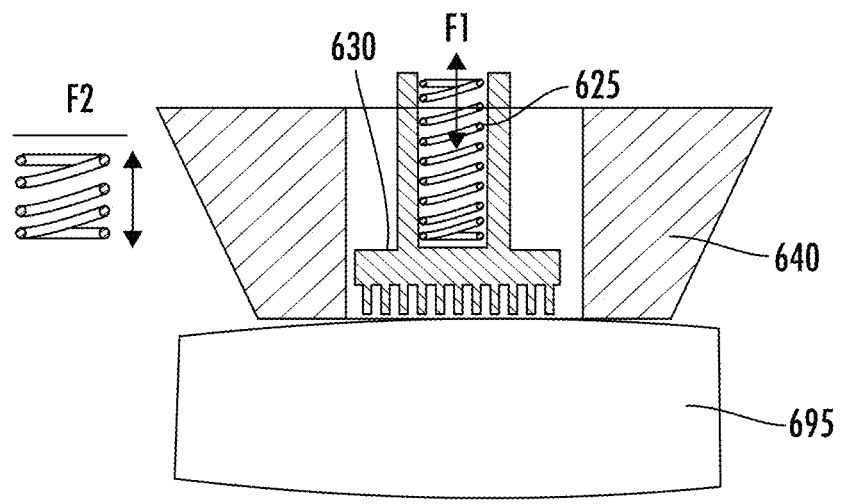
FIG. 6

BRAIN SIGNAL SENSING HEADSET

RELATED APPLICATIONS

This application is a continuation of International Application No. PCT/IB2022/057909, filed on Aug. 24, 2022, and entitled "Brain Signal Sensing Headset"; which claims priority to U.S. Provisional Patent Application No. 63/260,636, filed on Aug. 27, 2021, and entitled "Brain Signal Sensing Headset"; all of which are hereby incorporated by reference.

BACKGROUND

Brain cells communicate with each other by producing tiny electrical signals. Some amounts of the tiny electrical signals produced by the brain cells are transferred to the scalp of a person. Electroencephalography ("EEG") headsets are used to acquire brain signal information from the surface of the person's head adjacent the brain, to noninvasively detect and quantify those tiny electrical signals. EEG is performed by placing multiple electrodes in contact with the scalp to receive those electrical signals present on the scalp. The accuracy of EEG can be affected by a number of factors including electrode placement locations, integrity of electrode-to-scalp contact, electrical interference, and others.

EEG headsets have many applications, and the number of applications continues to expand. For example, EEG headsets have long been used in medical applications, and have typically been used in a medical facility where they are applied to the subject by trained medical personnel. One common example of an EEG headset used in medical applications is a standard EEG skullcap, which includes a cap made of a rubber or rubber-like material that is put on the subject's head like a swimming cap. The cap has numerous surface electrodes positioned throughout the cap in a manner such that they come in contact with surface of the subject's head. EEG headset designs like the standard EEG skullcap that cover the entire head have general applicability, and thus can be used for many different applications. Other types of EEG headsets have one or more arms that extend over the subject's head, such as from ear to ear similar to audio headphones, or extending outward from the top of the subject's head, or circumferentially around their forehead. The number and placement of electrodes for EEG headsets can also vary and be customized for the individual's physiology and for the usage application.

Brain signal sensing headsets may also use other forms of sensors, or in other words signal acquisition components, to acquire signals informative of electrical brain signal activations. One such form of sensor is a near infrared spectroscopy ("NIRS") sensor which acquires signals with hemodynamic information, in other words, information regarding the flow of blood—wherein the hemodynamic information is associated with or caused by electrical brain signal activations.

One application for brain signal sensing headsets is an area referred to as brain computer interface (BCI) or brain machine interface (BMI) applications. In a BCI or BMI system, brain signals are acquired from either an implanted or surface brain signal sensing assembly, and processed in a computing system that ascertains the intent of the subject. Generally, the use of a BCI system includes a screening or learning mode in which the BCI system learns the brain signals a subject produces when thinking about or performing some specific thing, followed by an operation or chronic mode in which the BCI system continuously monitors brain signal information obtained using the electrode assembly to detect the presence of the learned brain signals, thus informing the BCI system of the subject's intentions. In the context of such a BCI system using non-implanted electrodes like a brain signal sensing headset, it is challenging to ensure that the signal capture components, or in other words the sensing components, are placed in the same position every time the system is used, including for example in multiple sessions of operational use. In addition, there are other areas beyond BCI systems where the signal capture component or sensor placement during multiple different sessions is important.

An area of use for brain signal sensing systems, such as EEG-based BCI systems, is for stroke patients. In many cases, stroke patients may only have the use of one arm and hand. In addition, it may be desired to have stroke therapy rehabilitation utilizing a BCI system to be performed outside of a rehabilitation clinic such that there may be no assistance available to the stroke patient in putting on the BCI system, including the headset. Thus, it is important to design brain signal sensing headsets to enable stroke patients to be able to put the headsets on by themselves using only one arm and hand while also ensuring that the sensor positioning is consistent from one session to the next.

SUMMARY

In some embodiments, devices for recording brain activity of a subject include a first arm shaped to extend along a subject's head, the first arm having a first pair of rails along a length of the first arm. The first pair of rails borders a first aperture that allows access to the subject's head, and the first pair of rails has grooves along interior edges facing the first aperture. The device includes an electrode assembly that has multi-directional adjustability in orientation. The electrode assembly includes a shell with tabs protruding from opposite sides of an outer surface of the shell, the tabs being rotatable with respect to the shell; a sleeve inside the shell, the sleeve having a clearance between the sleeve and the shell to allow angular tilting of the sleeve within the shell; an elastic element attaching a first end of the sleeve to an interior end of the shell; and an electroencephalography electrode removably inserted into the sleeve, with a contact surface of the EEG electrode facing the subject's head. The electrode assembly is mounted in the first arm, with the tabs slidably seated in the grooves of the first pair of rails. The device also includes a housing having a bottom surface facing the subject's head, where the housing contains an energy source and electronic circuitry for the electrode assembly; and a second arm removably coupled to the housing, the second arm extending along the subject's head. The first arm is removably coupled to the housing and extends along the subject's head in a direction different than the second arm.

In some embodiments, a device for recording brain activity of a subject includes a plurality of electrode assemblies. Each electrode assembly has multi-directional adjustability in orientation and includes: a shell with tabs protruding from opposite sides of an outer surface of the shell, the tabs being rotatable with respect to the shell; a sleeve inside the shell, the sleeve having a clearance between the sleeve and the shell to allow angular tilting of the sleeve within the shell; an elastic element attaching a first end of the sleeve to an interior end of the shell; and an electroencephalography electrode removably inserted into the sleeve, with a contact surface of the EEG electrode facing a subject's head. The device also includes a housing having a bottom surface, a first lateral edge, and a second lateral edge, wherein the housing contains an energy source and electronic circuitry for the plurality of electrode assemblies. A first arm is removably coupled to the housing and shaped to extend along the subject's head from the first lateral edge of the housing, the first arm having a first pair of rails along a first length of the first arm. The first pair of rails borders a first aperture that allows access to the subject's head, and the first pair of rails has first grooves along interior edges facing the first aperture. A second arm is removably coupled to the housing and is shaped to extend along the subject's head from the second lateral edge of the housing. The second arm has a second pair of rails along a second length of the second arm, wherein the second pair of rails borders a second aperture that allows access to the subject's head. The second pair of rails has second grooves along interior edges facing the second aperture. A third arm is removably coupled to the housing, the third arm extending along the subject's head in an anterior-to-posterior direction. A first electrode assembly of the plurality of electrode assemblies is mounted in the first aperture of the first arm, the tabs of the first electrode assembly being slidably seated in the first grooves of the first aperture. A second electrode assembly of the plurality of electrode assemblies is mounted in the second aperture of the second arm, the tabs of the second electrode assembly being slidably seated in the second grooves of the second aperture.

In some embodiments, devices for recording brain activity of a subject include a first arm shaped to extend along a subject's head, the first arm having a first aperture that allows access to the subject's head. A sensor assembly of the device has multi-directional adjustability in orientation. The sensor assembly includes a shell configured for multi-directional rotation; a sleeve inside the shell; an elastic element attaching a first end of the sleeve to an interior end of the shell; and a sensor removably inserted into the sleeve, with a contact surface of the sensor facing the subject's head. The device also includes a housing that contains an energy source and operational components for the sensor assembly.

BRIEF DESCRIPTION OF THE DRAWINGS

FIGS. 3A-3C are isometric and exploded views of electrode assemblies, in accordance with some embodiments.

FIGS. 4A-4E are cross-sectional views of electrode assemblies showing multi-directional adjustability, in accordance with some embodiments.

FIG. 5A is a bottom perspective view of an electrode assembly with an insertable electrode, in accordance with some embodiments.

FIG. 5B is an isometric view of the electrode of FIG. 5A.

FIG. 6 is a cross-sectional view of a compressible pad surrounding an electrode assembly, in accordance with some embodiments.

DETAILED DESCRIPTION

Brain signal sensing headsets such as EEG headsets are disclosed that have unique sensor positioning mechanisms, ensuring accurate and repeatable sensor (e.g., electrode) placement along with high integrity contact with the subject's head. Embodiments also enable easy usage, allowing a patient to don the headset and even replace individual sensors in the headset with one hand. In addition, the disclosed headsets are modular in design, enabling customizable functionality and accommodation of different head sizes and shapes. The brain signal sensing headsets disclosed herein may be used in any application that requires such headsets such as brain computer interface (BCI) applications. In a particular example, the headsets may be used in BCI applications for stroke therapy, such as using the headset to obtain ipsilateral and/or contralateral brain signals.

Embodiments shall be described primarily for EEG electrodes that are insertable into the brain sensor headsets. However, embodiments can also be applied to other types of sensors for monitoring or measuring brain activity, such as electromagnetic or light sensors (e.g., infrared or near-infrared sensors, such as near-infrared spectroscopy). Accordingly, references to an electrode or EEG electrode in this disclosure shall apply to other types of sensors. Similarly, electrical components and connections for EEG electrodes described herein can be substituted with components and connections for other types of sensors that are used with the brain sensor headsets.

Figure 1A:
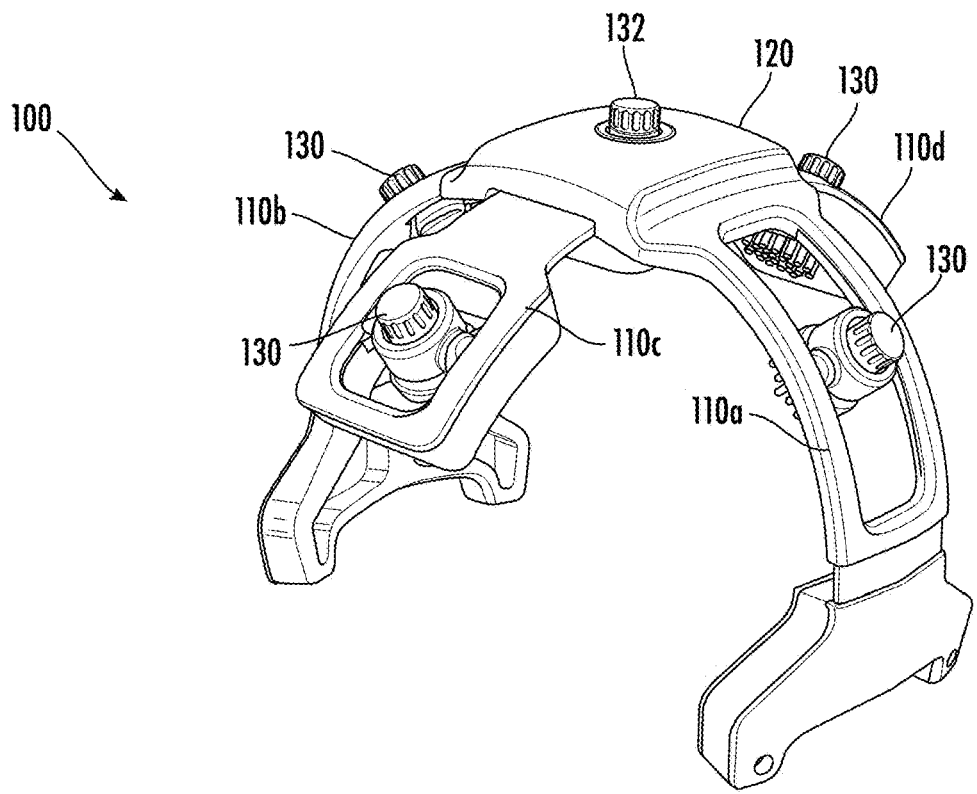
FIGS. 1A-1C provide isometric and front views of an EEG headset, in accordance with some embodiments.
Figure 1B:
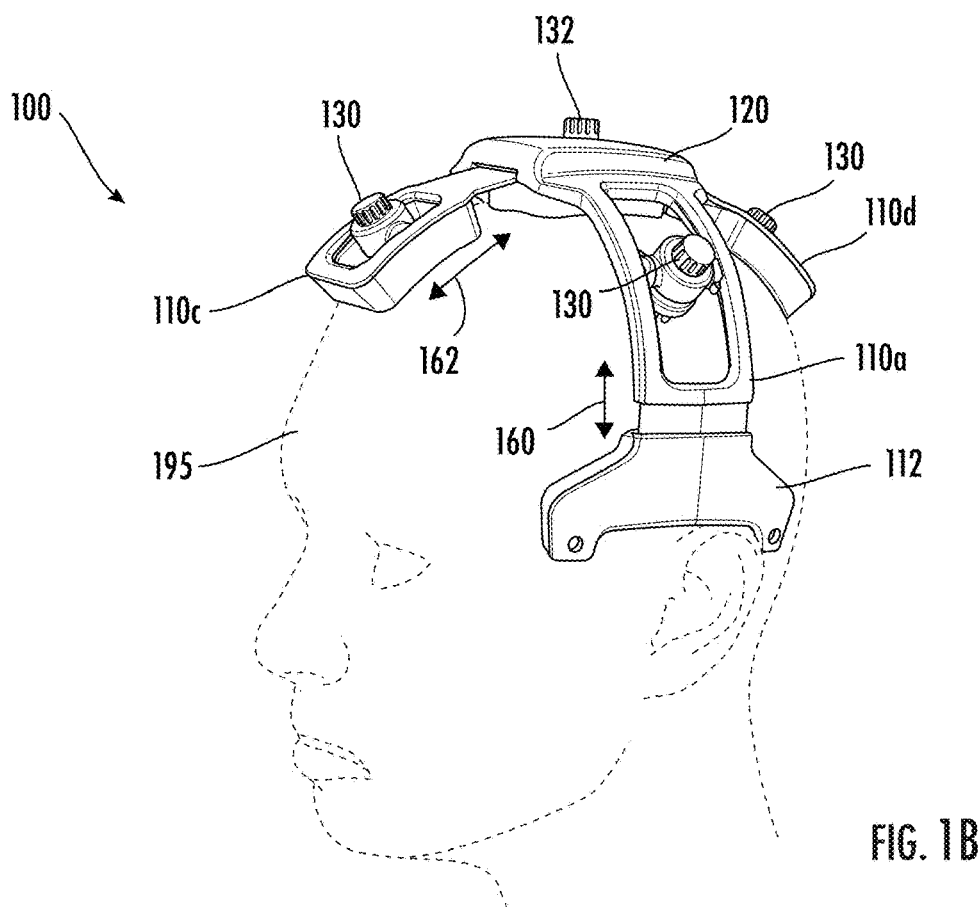
Figure 1C:
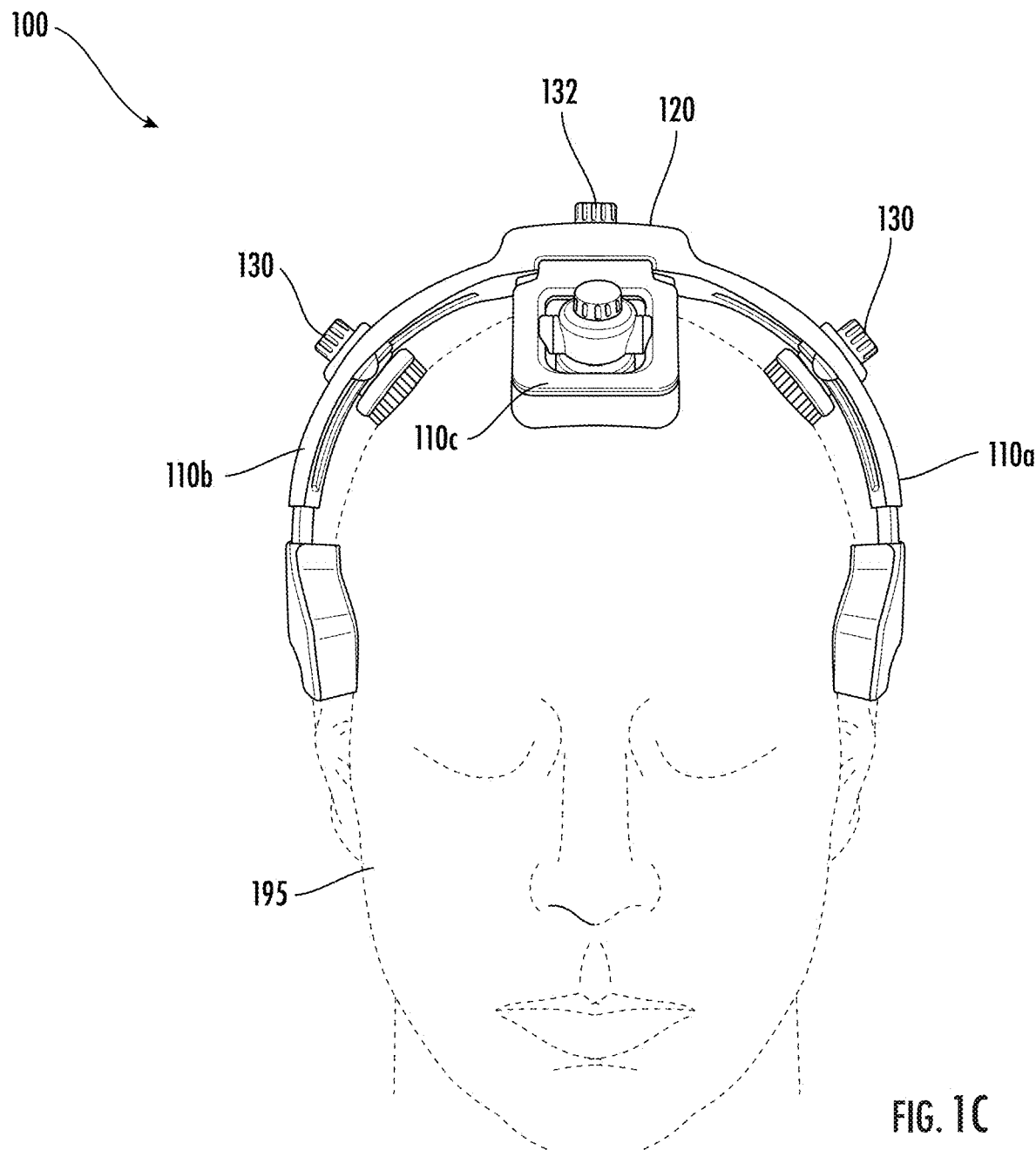

FIGS. 1A-1C show various views of a brain sensor headset, illustrated as an EEG headset 100, in accordance with some embodiments. FIG. 1A provides an isometric view of the headset 100 alone, while FIGS. 1B and 1C show side and front views, respectively, of the headset 100 on a patient's head 195. The headset 100 includes multiple arms 110*a-d* that extend from a central housing 120. The arms 110*a-d* extend along the subject's head in different directions from each other and are removably coupled to the housing 120, providing a modular design. Brain signals are collected by multiple electrode assemblies 130 (or other type of sensor) that are mounted in the arms 110*a-d* that extend along the subject's head. The electrode assemblies 130 are movable along the arms and are adjustable in orientation with respect to the subject's head. Brain signals are also collected by an electrode 132 that is fixedly mounted in the central housing 120. The housing 120 contains components (not shown in this figure) to operate the electrode assemblies 130 and electrode 132, such as electronic circuitry and one or more energy sources. The energy source may be a battery in some embodiments, and the electronic circuitry can include, for example, amplifiers and analog-to-digital (A/D) converters.

The headset 100 may be adjustable in the overall length and positioning of the arms to accommodate different head sizes and applications. For example, arrow 160 in FIG. 1B indicates that arm 110a may be slidable with respect to distal plate 112 of the arm 110a, such that the arm 110a lengthens as it telescopes out from distal plate 112. The sliding interaction may involve securing features and tactile feedback, such as ratchet-type tracks having notches that hold the arm 110a in position after it is moved. The distal plate 112 is shown as being seated just above or resting on the upper edge of the patient's ear in this embodiment. In other embodiments, the distal plate 112 can cover the ear, or can be spaced apart from the ear. Arrow 162 indicates that arm 110c is also movable. In some embodiments, arm 110c can telescope out from housing 120. In other embodiments, arms 110c and 110d may be formed as one piece (e.g., a "headband") that slides relative to housing 120, such that as the forward arm 110c moves anteriorly (more toward the subject's forehead), rear arm 110d moves in the same direction with it.

Figure 2A:
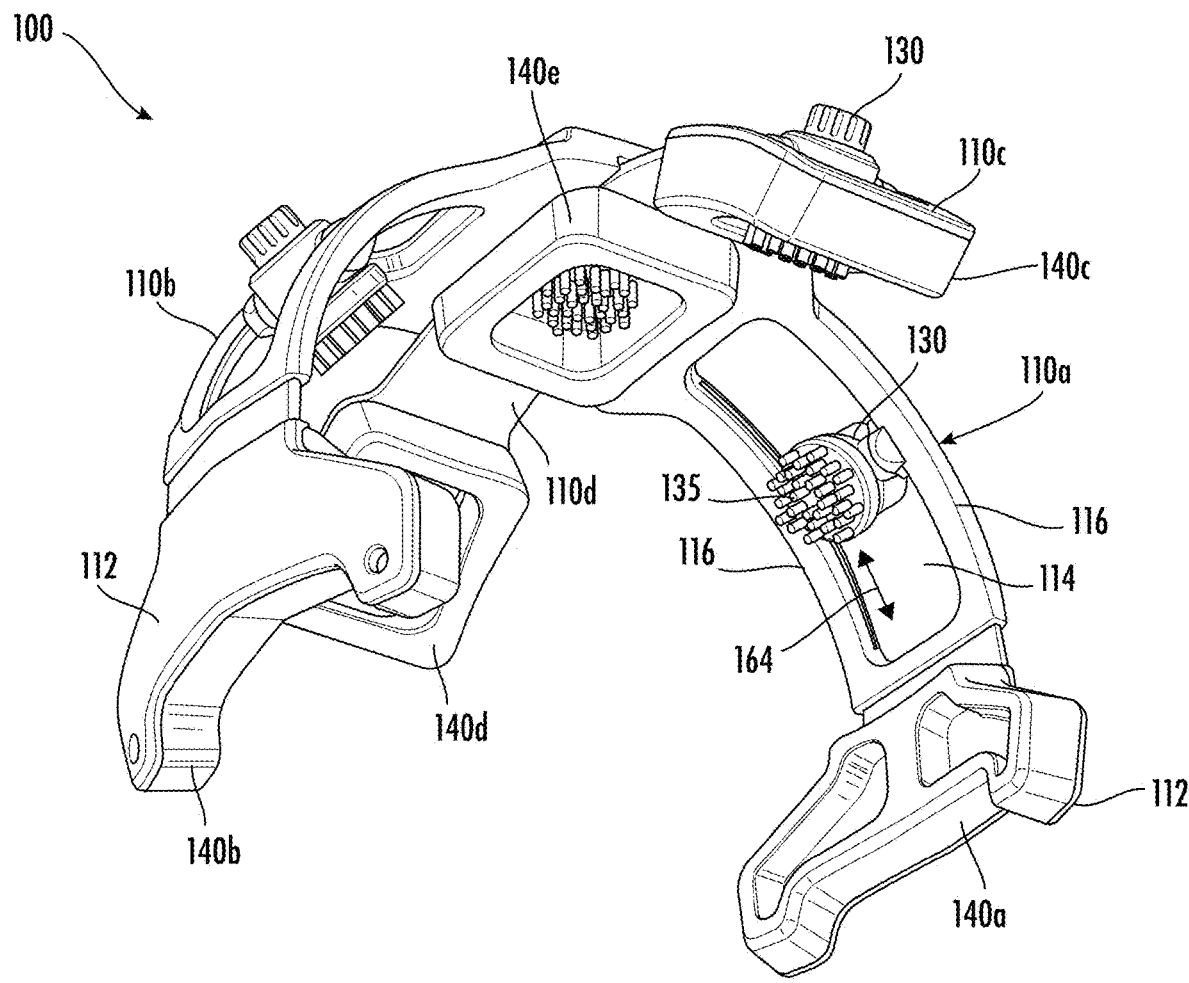
FIG. 2A is a bottom isometric view of an EEG headset, in accordance with some embodiments.

FIG. 2A shows a bottom isometric view of the headset 100, showing pads 140a-e that may be included on the headset 100 to provide comfort. For example, pads 140a-e may be made of a compressible material such as foam, elastomers, or other polymeric materials. Pads 140a-e may be configured to be replaceable if the pads become soiled or worn, such as by being attached to the headset 100 with mechanical fasteners such as hook-and-loop fasteners, snaps or clips. Pads 140a and 140b are on the distal plates 112 of arms 110a and 110b respectively, facing the subject's head to provide cushioning when the subject wears the headset 100. Pads 140c and 140d are at distal areas of arms 110c and 110d, respectively, on an underside of the arms to face the subject's head, and surrounding (i.e., forming a perimeter or border around) electrode assemblies 130 that are mounted in those arms. Pad 140e is on a bottom surface of housing 120 and surrounds electrode 132 (FIG. 1A). Pads 140c, 140d and 140e can be configured not only to provide cushioning, but also to provide electromagnetic interference (EMI) shielding for the electrodes surrounded by the pads. Pads 140c, 140d and 140e can serve as EMI shields by being configured to function as a Faraday cage to reduce the negative impacts of EMI and radio frequency interference (RFI) on the fidelity of the EEG signals detected from the user. Such shielding may eliminate inaccuracies in the EEG results by isolating the EEG electrode signals from ambient electrical noise.

In some embodiments, the pads (e.g., pads 140c, 140d and/or 140e) can include a metal screen or mesh material to create the EMI shielding. For example, a copper (or other conductive metal) screen or mesh may be used. In such embodiments, the metal screen or mesh material may be overmolded during the formation of the pads. Alternatively, the metal screen or mesh material may be attached to the pads after or while the pads are formed. In some embodiments, a conductive coating is applied to the pads to provide the EMI shielding. For example, the conductive coating can include small metallic particles (e.g., copper or nickel) that are dispersed in a suitable carrier material. The dispersion can be sprayed, brushed, or otherwise coated onto the pads. In some embodiments, the EMI shield can comprise a combination of the metal screen or mesh material and the conductive coating(s). In particular embodiments, the EMI shielding in the pads is configured to be an active shield (e.g., a negative capacitance circuit).

Figure 2B:
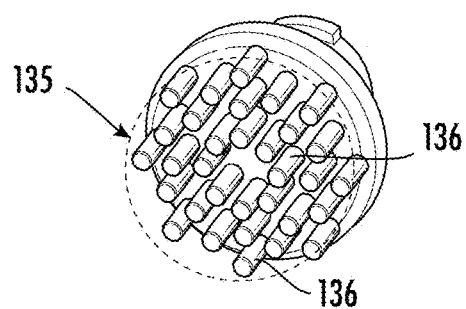
FIG. 2B is a bottom view of an electrode from FIG. 2A, in accordance with some embodiments.

FIG. 2A also shows contact surface 135 of the electrodes. Contact surface 135, shown in a close-up view in FIG. 2B, is the portion of the electrode that will contact the subject's head. There are different types of standard EEG electrodes, two main categories being wet or dry electrodes. Wet electrodes use gel to facilitate electrical contact of the electrode to the scalp through the person's hair, and often have a disk shape (e.g., cup electrodes). For dry EEG electrodes, electrodes often include a plurality of fingers, sometimes referred to as a "comb" configuration. An embodiment of a dry electrode is illustrated with fingers 136 in FIG. 2B, where the tips of fingers 136 that face the subject's head collectively define the contact surface 135. Fingers 136 are arranged in concentric rings in a circular area of in this embodiment, but may be arranged in other geometric patterns in other geometrically shaped areas in other embodiments. The fingers 136 can penetrate a person's layer of hair, and therefore facilitate contact with the scalp without the need for gel.

Electrode 132 of FIGS. 1A-1C is fixedly mounted in housing 120. Because housing 120 is located on the top of a person's head, electrode 132 will inherently be perpendicular to the scalp and have good physical and electrical contact. In contrast, electrode assemblies 130 are positioned on other portions of a person's head, such as on the lateral, anterior and posterior areas where the head's curvature will vary on the individual and from person to person. FIG. 2A illustrates that the electrode assemblies 130 are repositionable within the headset arms, enabling customization in accommodating different sizes and shapes of heads, as well as different electrode configurations (e.g., number of electrodes and various placements) for different applications. For example, arrow 164 in FIG. 2A indicates that electrode assembly 130 is slidable along the length of aperture 114 of arm 110a. Aperture 114 is an opening along the length of arm 110a, allowing access to the subject's head. Aperture 114 is formed by the pair of rails 116 on opposite sides of the aperture 114. Movement of the electrode assembly 130 along the rails 116 enables adjustability in the positioned location of the electrode assembly 130 on the subject's scalp.

Because the curvature of a person's head varies around its surface, repositioning of the electrodes around the subject's head can affect the integrity of the electrode-to-scalp contact. That is, contact surface 135 of an electrode may not remain in full contact with the person's head if the electrode is simply slid from one point to another along arm 110a. For the multi-finger electrode configuration of FIG. 2B, because the ends of the fingers 136 create essentially a planar contact surface 135, it is important for the electrode to be perpendicular to the subject's head in order for most or all of the fingers 136 to have contact with the subject's scalp.

Embodiments of sensor assemblies (e.g., electrode assemblies) have multi-axis adjustability in orientation to enable consistent contact of the sensors (e.g., electrodes) with a user's head, compensating for different head shapes and various placement locations of the electrodes on the head. In some embodiments, a shell of a sensor assembly is configured for multi-directional rotation such as angular tilting with respect to the Z-axis perpendicular to the subject's head and rotation about a Y-axis perpendicular to the Z-axis. The sensor is removably inserted into a sleeve that is attached by an elastic element to an interior end of the shell, thereby also enabling movement of the sensor along the Z-axis. Embodiments also enable easy replacement of electrodes even if the user only has the use of one hand or arm. EEG electrodes, such as fingers 136, are often made of silver/silver-chloride (Ag/Ag—Cl) which can wear out over time, and therefore need to be replaced periodically.

FIGS. 3A-3C are side isometric views of an electrode assembly 300, which corresponds to electrode assemblies 130 of FIG. 1A. The electrode assembly 300, in some embodiments, may be an assembly comprising other types of sensors for brain signal sensing, such as electromagnetic or light sensors. FIG. 3A is an exploded view prior to an electrode 330 being inserted into the rest of the electrode assembly 300, FIG. 3B shows an accessory knob 350 on the electrode assembly 300, and FIG. 3C shows the electrode assembly 300 with the electrode 330 inserted. Electrode assembly 300 includes a shell 310, the electrode 330, and the optional accessory knob 350. Electrode 330 is insertable into sleeve 320 which fits into the shell 310, enabling replacement of electrode 330 such as when the silver/silver-chloride fingers 336 degrade. In other words, electrode 330 is received by sleeve 320 which is inside shell 310. Knob 312 of shell 310 enables rotation of the electrode 330 about a Z-axis 390 that runs along an axial direction of the shell 310. Accessory knob 350 has a larger diameter than knob 312 for users that have low dexterity and may be placed on knob 312 to facilitate rotation of the electrode 330 about the Z-axis 390 as indicated by arrow 392. Also shown in FIG. 3A is a wire 370 for electrical connection of the electrode 330 to the EEG headset.

Figure 4A:
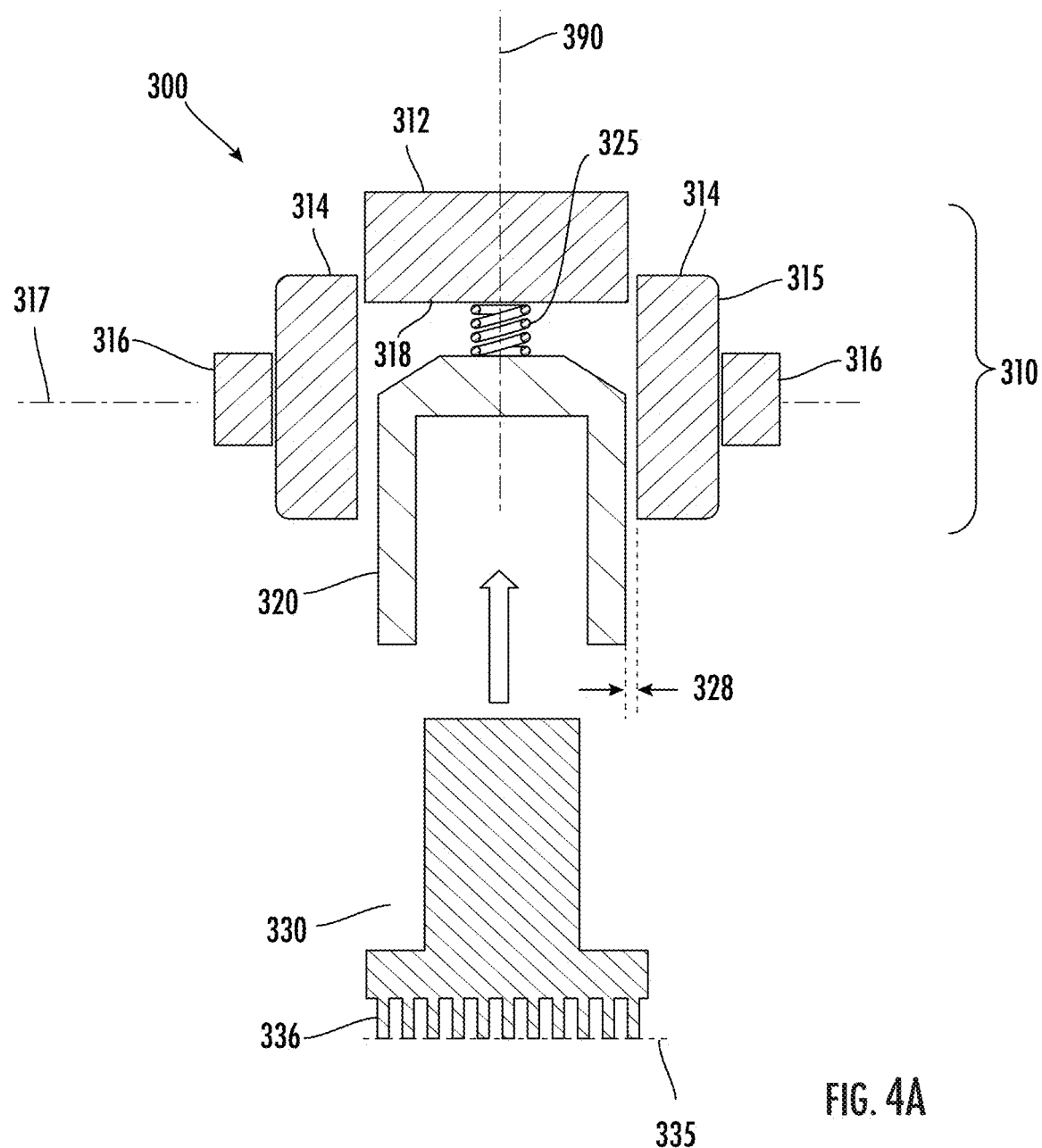
Figure 4B:
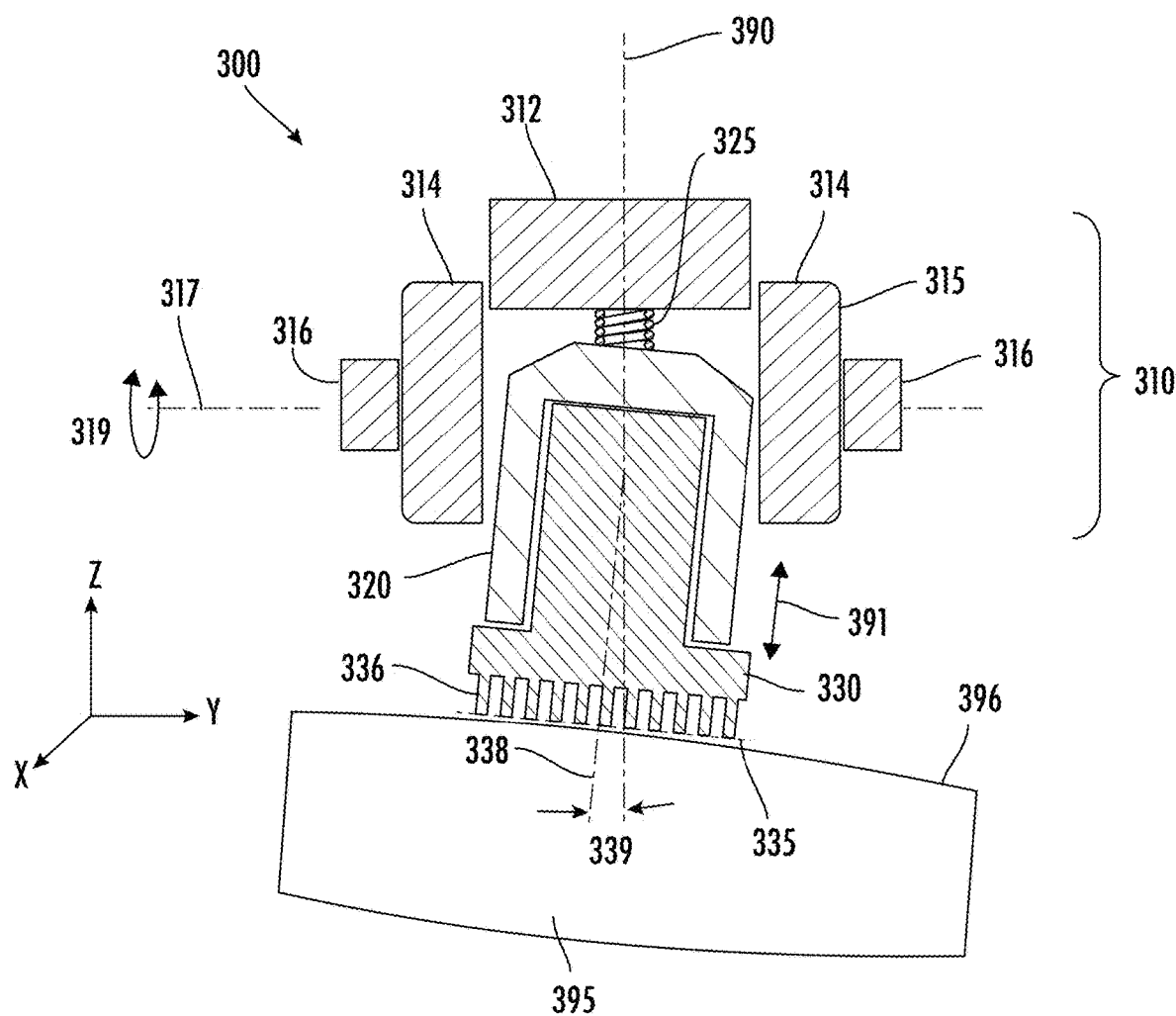

FIGS. 4A and 4B are vertical cross-sectional views providing further detail about the multi-directional adjustability of the sensor assemblies, such as electrode assemblies, in accordance with embodiments. Shell 310 includes knob 312, walls 314 and tabs 316 that protrude from opposite sides of outer surface 315 of walls 314. Sleeve 320 is inside shell 310, attached by an elastic element 325 to an interior end 318 of shell 310. Elastic element 325 may be, for example, a spring, flexible polymer (e.g., elastomer such as foam or rubber), or other material that allows linear movement of sleeve 320 within shell 310 along the Z-axis 390, as well as angular movement with respect to Z-axis 390. The Z-axis 390 is perpendicular to Y-axis 317 that runs through tabs 316, and consequently is also perpendicular to the headset arm (not shown) when mounted into the overall EEG headset. Electrode 330 is removably insertable into the sleeve 320, with the ability of being locked into the sleeve 320 after it is inserted. Sleeve 320 has a clearance 328 between the exterior of the sleeve 320 and interior of the shell 310, allowing the sleeve 320 to tilt angularly with respect to the Z-axis 390, as shown in FIG. 4B.

FIG. 4B demonstrates the ability of the electrode 330 to adjust its orientation so that the electrode 330 can have proper contact with a subject's head 395. In FIG. 4B, electrode 330 is loaded into the electrode assembly 300, and the electrode 330 is positioned on surface 396 of the subject's head 395. The clearance 328 (FIG. 4A) enables the central axis 338 of the sleeve 320 and electrode 330 to tilt at an angle 339 relative to the Z-axis 390 of shell 310 to accommodate the curvature of the surface 396. Ideally, the central axis 338 of the electrode 330 will be perpendicular to the surface 396 of the user's head 395 to optimize contact between the surface 396 and the contact surface 335 formed by fingers 336. The angular tilt (angle 339) can be omnidirectional (i.e., 360° spherical movement) around Z-axis 390 similar to a universal ball joint, thereby enabling versatility in the orientation of the electrode 330. In some embodiments, a ball joint, wire or other attachment mechanism (e.g., plunger 326 in FIG. 4C) can be included along with elastic element 325 to provide mechanical redundancy in the coupling of sleeve 320 to shell 310 while also allowing angular adjustability.

Clearance 328 is designed to allow an angular tilt 339 of, for example, up to 20°, such as ±20°, ±10°, or ±5° of the sleeve 320 with respect to Z-axis 390. The "floating" of the sleeve 320 within the electrode assembly 300 is enough to accommodate variations in curvature along a person's head or from individual to individual, but small enough to maintain secure positioning of the electrode on the person's head. The amount of clearance to achieve these angles will depend on the outer diameter of the sleeve 320, inner diameter of the shell 310, and length of the shell's cavity that holds the sleeve 320. For example, for larger sized components or for electrodes that are seated deeper into the sleeve, more clearance may be required to achieve the same amount of angular tilting. In some embodiments, clearance 328 may be, for example, up to 5.0 mm, such as 1.0 mm to 5.0 mm, or 2.0 mm to 4.0 mm, or 0.5 mm to 1.5 mm, or up to 1.0 mm. In some embodiments, different electrode assemblies within a headset may be designed with different ranges of angular tilting. For example, a person's head often has more curvature in the forward/back direction than on the sides. Accordingly, some embodiments of the EEG headset can be configured with electrode assemblies having a greater amount of angular adjustability on the anterior and posterior arms (e.g., arms 110c and 110d of FIG. 1A) than the electrodes on the lateral arms (e.g., arms 110a and 110b). The electrode 330 can be a universally sized electrode such that the same type of electrode 330 fits into any of the electrode assemblies.

Besides being tiltable with respect to the Z-axis, further multi-axis adjustment of the electrode 330 is provided by tabs 316. In FIG. 4B, tabs 316 are rotatable with respect to the walls 314 of shell 310, about the Y-axis 317, which allows the entire electrode assembly 300 to swivel about the Y-axis 317 as indicated by arrow 391. Additionally, electrode 330 is linearly movable along its central axis 338 as indicated by arrow 391 due to the elastic element 325. For example, FIG. 4B shows elastic element 325 being compressed compared to in FIG. 4A, consequently retracting the electrode 330 and sleeve 320 further into shell 310 compared FIG. 4A. This ability of the electrode 330 to extend in and out of shell 310, in addition to the angular adjustments about the Z-axis 390 and Y-axis 317, uniquely facilitate proper contact of the contact surface 335 of electrode 330 with surface 396 of the patient's head 395 without the need for detailed adjustments by the user. In some embodiments, the electrode assembly 300 is self-adjusting. That is, the electrode 330 within electrode assembly 300 naturally adapts its orientation to the curvature of the subject's head due to the "floating" of the sleeve 320 within the electrode assembly 300 and the ability of the electrode assembly 300 to pivot via tabs 316. In some embodiments, the subject may use one hand to adjust the electrode assembly 300, to help ensure that the fingers 336 are penetrating through their hair. However, the need for tools or two hands of the user are not required since the electrode assembly 300 is beneficially designed with multiple degrees of freedom in orientation adjustment. Furthermore, the rotation of knob 312 about the Z-axis 390 enables one-handed rotation of the fingers 336 about central axis 338, such as to help the fingers 336 penetrate hair or to provide more positional adjustability.

FIG. 4C shows another embodiment of an electrode assembly 301 in two positions/orientations. In this embodiment, the electrode assembly 301 includes a plunger 326 placed inside and parallel to elastic element 325 (illustrated as a coil spring in this embodiment). The plunger 326, in addition to elastic element 325, couple the sleeve 320 and consequently electrode 330 to knob 312. State (I) shows the sleeve 320 and electrode 330 aligned vertically along the Z-axis 390 of the shell 310 and extended axially downward from the shell 310. State (II) shows the sleeve 320 and electrode 330 tilted at an angle 339 with respect to the Z-axis 390, with the sleeve 320 and electrode 330 retracted into the shell 310 as indicated by arrow 360. The tilt angle 339 of state (II) demonstrates the ability of the electrode assembly 301 to adjust for the curvature of the subject's head. The telescoping in and out of the shell 310 per arrow 360 demonstrates the ability of the electrode assembly 301 to adjust for the distance of a subject's head to the electrode 330, with the subject's head being closer to the electrode 330 in state (II) compared to state (I) in this illustration.

FIGS. 4D and 4E are cross-sectional views of embodiments similar to FIG. 4C, but with alternative elastic elements 325. In the electrode assembly 302 of FIG. 4D, elastic element 325 is made of an elastomer (e.g., polyurethane, silicone, and the like) in the form of a cylinder with open slots within its walls. Elastic element 325 couples the sleeve 320 and consequently electrode 330 to knob 312, the same as the coil spring elastic element 325 of FIG. 4C. State (I) of FIG. 4D is with the sleeve 320 and electrode 330 aligned vertically along the Z-axis 390 and extended axially downward from the shell 310. State (II) shows the sleeve 320 and electrode 330 tilted at an angle 339 with respect to the Z-axis 390, with the sleeve 320 and electrode 330 retracted into the shell 310 as indicated by arrow 360. As can be seen in state (II) of FIG. 4D, the slots of elastic element 325 are shortened compared to the state (I), due to the compression of the elastic element 325. FIG. 4E shows an electrode assembly 303 in a similar state as FIG. 4D state (II), but with yet another embodiment of an elastic element 325. Elastic element 325 is configured as a cylinder with solid walls, which bulges outward when compressed.

FIGS. 5A and 5B illustrate lockable insertion of the electrodes into electrode assemblies, in accordance with some embodiments. FIG. 5A is a bottom isometric view of an electrode 530 being inserted into an electrode assembly 500, and FIG. 5B is a side isometric view of the electrode 530. Electrode 530 has protrusions 532 extending from the end of shaft 534 that is inserted into the electrode assembly 500. The shaft is a cylindrical body in this embodiment. In this embodiment, electrode 530 has two protrusions 532, but other numbers of protrusions are possible such as only one protrusion, or more than two. Protrusions 532 fit into detents 522 of sleeve 520, and when the shaft 534 of electrode 530 is fully inserted into sleeve 520, the user turns the electrode 530 so that the detents 522 are secured into groove 524 at the interior face of the sleeve 520. Thus, the EEG electrode 530 is removably inserted into the sleeve 520 with a turn-locking mechanism, the EEG electrode 530 having a cylindrical body with a protrusion 532 that mates with a recess (groove 524) in an interior of the sleeve. The sliding of the shaft 534 into the sleeve 520 and the turn-locking motion is easily manageable with one hand. For example, the user can lay the headset in their lap and insert the electrodes into the electrode assembly 500 with one hand, inserting and turning the electrode 530 into the sleeve 520. In various embodiments, the electrode 530 can involve a partial rotation to lock the electrode into place, such as a quarter-turn rotation (approximately 90°), or a half-turn rotation (approximately 180°), or other degrees of rotation that are greater or less than a quarter or half turn. As mentioned above, the floating of the sleeve 520 within the electrode assembly 500 provides enough movement to allow angular adjustment but is limited enough to be secure. Thus, the turn-locking motion by a user to insert the electrodes into the headset is achievable by one hand. Removal of the electrodes is similarly achievable with one hand.

In other embodiments, turn-locking configurations other than that shown in FIGS. 5A-5B may be utilized. For example, the rectangular protrusions 532 and detents 522 may be substituted with a bayonet mount or other types of quarter-turn fastening features. In further embodiments, non-rotating mechanisms may be used that enable one-handed insertion and removal of the electrode 530 from the electrode assembly 500. For example, instead of a turn-locking mechanism, the sleeve 520 may include spring-loaded buttons that lock the detents 522 into the sleeve, and that release the detents when the buttons are pushed. In another example, the sleeve 520 may include a hinged latch that secures onto a lip or other geometrical feature of the electrode.

FIG. 5B shows that electrode 530 has electrical traces 572 on a top surface of the shaft 534. In this embodiment, the electrical traces 572 are concentric circles that correspond to the concentric ring arrangement of the fingers 536. When the electrode 530 is inserted into the sleeve 520, the traces 572 contact pogo pins 574 at the end face inside the shell. Pogo pins 574 may be spring-loaded to ensure reliable contact with the traces 572. Multiple pogo pins 574 are arranged in a linear array, with one pogo pin 574 corresponding to each ring of the electrical traces 572. That is, the pogo pins 574 are spaced apart at the same distance as the electrical traces 572. Because of the concentric arrangement of electrical traces 572, the pogo pins 574 will always be in contact with the electrical traces 572 regardless of the rotational orientation of the electrode 530 when it is inserted into the sleeve 520. The pogo pins 574 are electrically connected with wire 370 (FIG. 3A) that then connects to the headset. Other types of connections between the electrode and sleeve are possible rather than pogo pins, such as socket-type connectors. In embodiments for other types of sensors, the electrical connections of FIG. 5B can be configured for the particular type of sensor being used (e.g., optoelectronic, electromagnetic).

FIG. 6 depicts an embodiment in which a compressible pad 640, which may correspond to the pads 140c, 140d and 140e of FIG. 2A, can be used in conjunction with the electrode assemblies. Pad 640 is designed to provide comfort while still ensuring adequate contact of the electrodes with the subject's skin. FIG. 6 is a simplified vertical cross-sectional schematic of an electrode 630 having a pad 640 surrounding the electrode 630 and facing the subject's head 695. The electrode 630 is pressed against the subject's head 695 with a first spring force F1 due to elastic element 625 (illustrated schematically to represent elastic element 325 of FIGS. 4A-4E), to which the electrode 630 is coupled. The pad 640 has a second spring force F2 due to the material of the pad 640. For example, the durometer of the material for pad 640 (e.g., a foam) is chosen to impart the desired spring force F2. In further embodiments, the material's durometer and/or its structure, such as the density of the cell structure of a foam, may be designed to achieve the target spring force F2. The material for pad 640 may be, for example, biocompatible open or closed cell foams such as polychloroprene, polyurethane, silicone, polyethylene or rubber. In some embodiments, the pad 640 may be made of a self-skinning material for ease of cleaning.

The pad 640 and electrode 630 are uniquely designed to work together to provide optimal stability, contact, and comfort for the user. The combination of the pad 640 with the electrodes 630 distributes the pressure felt by the subject.

In particular, the spring force F2 of the pad 640 is configured to be less than the spring force F1 of the elastic element 325 so that the electrode 630 can telescope in or out of the electrode assembly enough to make proper contact, but the pad 640 alleviates some of the force to improve comfort for the user. That is, the pad 640 yields more than the pressure of the electrode against the head, so that the pad takes some pressure off of the electrode. The pad 640 maintains the force of the electrode against the user's head, but distributes the weight to improve comfort. The overall surface area of the pad, such as a wide band forming a rectangular perimeter around the electrode as shown in FIG. 2A, can also provide stability of the electrode and headset on the user's head.

Figure 7A:
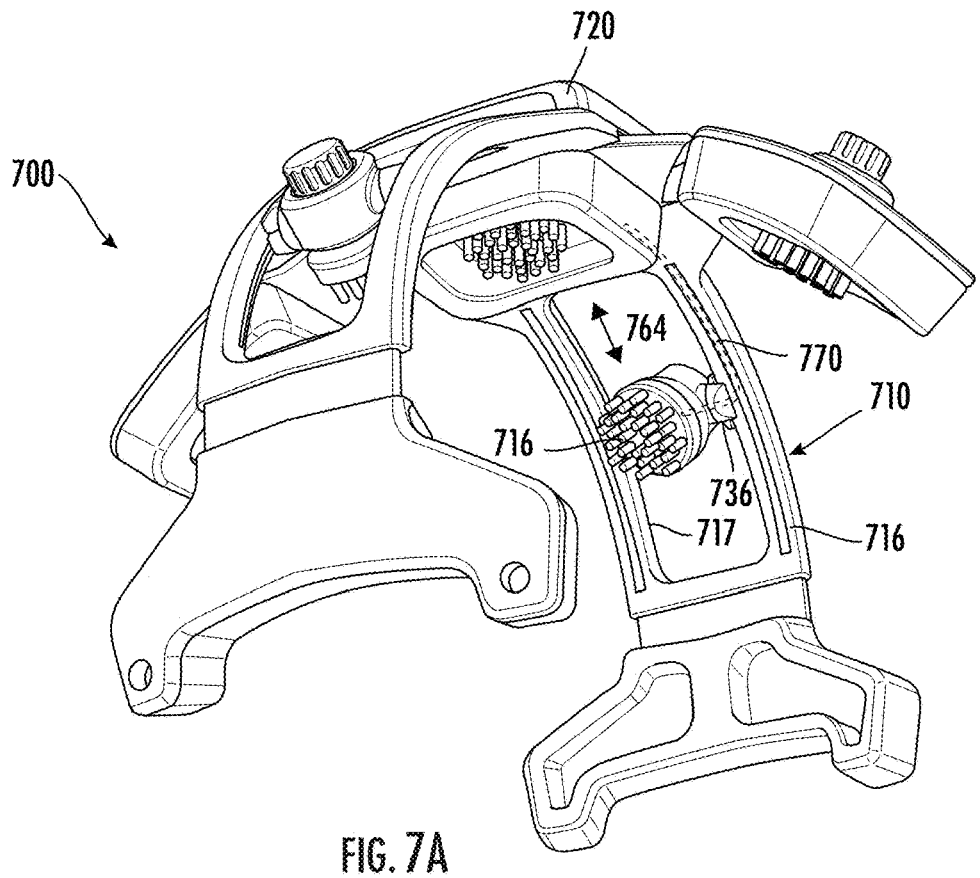
FIGS. 7A and 7B are perspective views of an EEG headset, showing wiring for electrodes in an EEG headset, in accordance with some embodiments.
Figure 7B:
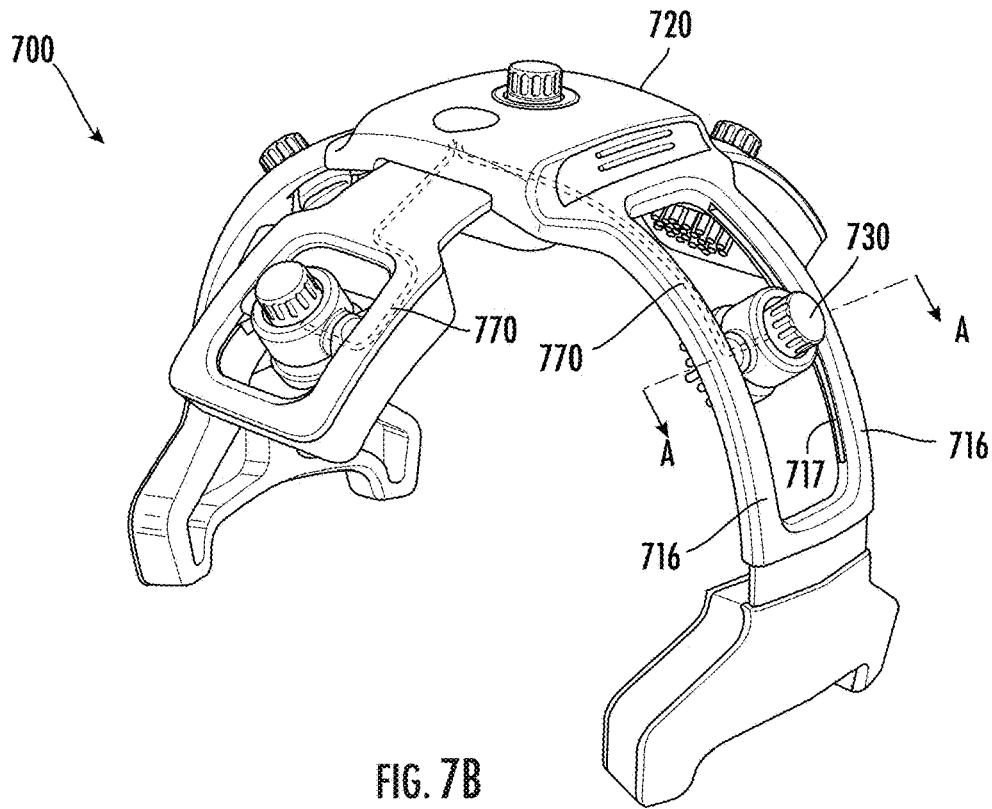

FIGS. 7A-7D illustrate how the electrode assemblies are physically mounted and electrically wired into the EEG headsets. FIG. 7A is a bottom isometric view and FIG. 7B is a top isometric view of an EEG headset 700 with an electrode assembly 730 mounted into rails 716 of arm 710. Specifically, tabs 736 of electrode assembly 730 are slidably seated in grooves 717 that run along the length of rails 716. The seating of the electrode assembly 730 in groove 717 of the rails 716 is shown in more detail in the cross-sectional view of FIG. 7C, taken along section A-A of FIG. 7B. Consequently, electrode assembly 730 can slide lengthwise along the arm 710 as indicated by arrow 764, to position the electrode assembly 730 as needed on the patient's head. Other embodiments are possible for coupling the electrode assemblies with the headset. For example, rather than being inserted into a groove, each tab 736 can be coupled to a band or clip that mounts onto and slides along the rail 716.

Initial placement of the electrode assembly 730 on a patient's head to acquire the desired brain signal may be performed by a medical professional (e.g., physical therapist or physician). When the proper location of the electrode assembly 730 has been determined, the electrode assembly 730 may be secured in position as a result of having a friction fit between the electrode assembly 730 and the rails 716, and/or by positive locking features such as set screws, clamps, spring-loaded engagement features, or notches along the rail (e.g., ratchet-type track). After the initial electrode locations have been set by the medical personnel, the user can don the headset on their own, without the need for assistance, since the design of the headset ensures consistent and repeatable contact of the electrodes with the targeted sites. In some embodiments, the headset can also include registration features to further enhance repeatable placement on the subject's head, such as features to engage with a subject's nasion and/or inion as described in U.S. Patent Publication No. 20170143228, "EEG Headsets with Precise and Consistent Electrode Positioning," owned by the assignee of the present disclosure.

Figure 7C:
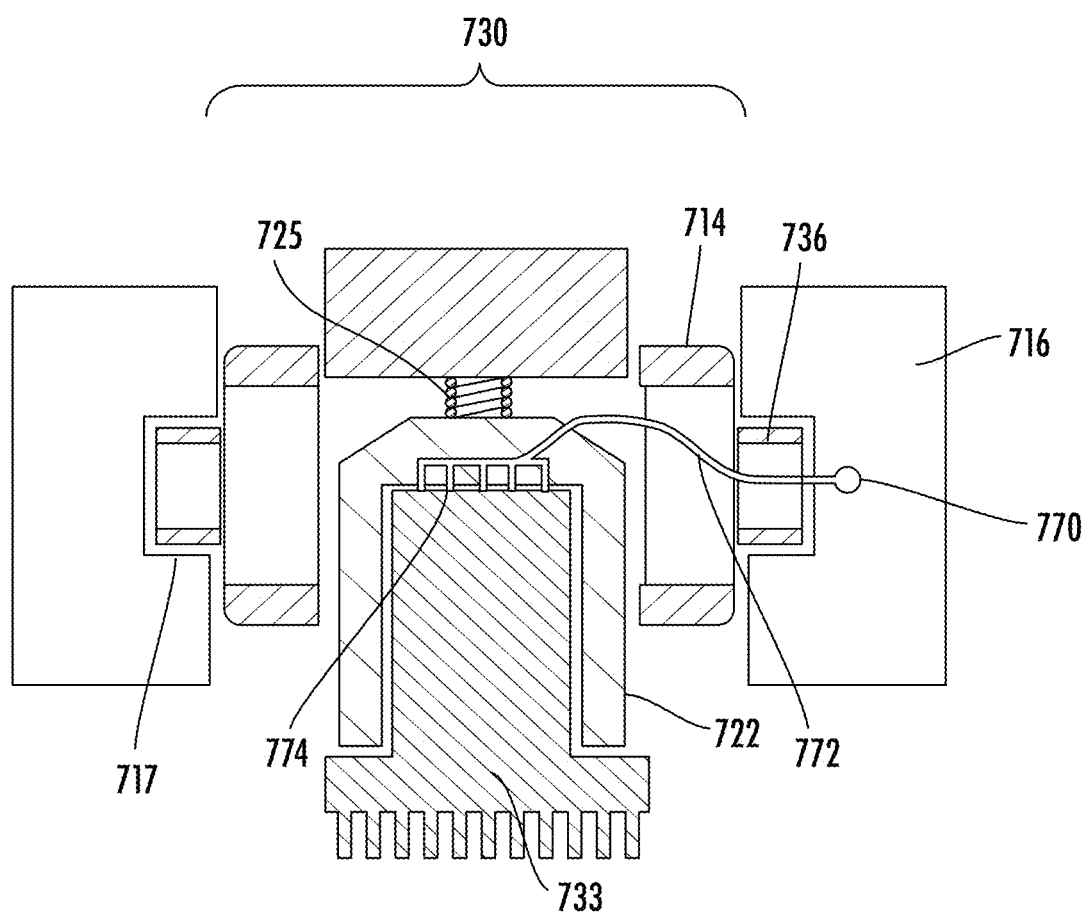
FIG. 7C is a cross-sectional view of wiring for electrodes, in accordance with some embodiments.

Also shown in FIGS. 7A-7D is the routing of electrical wires 770 from the electrode assemblies 730 to the housing 720. In FIGS. 7A-7B, wiring 770 (corresponding to wire 370 of FIG. 3A) from the electrode assemblies runs within rails 716 and connects to the housing 720, as will also be described in relation to FIGS. 8 and 9A-9B. The wiring 770 within rails 716 can include slack (extra length) to account for repositioning of the electrode assemblies along the headset arms. In FIG. 7C, internal electrical wiring 772 within the electrode assembly 730 runs from the sleeve 722 through one of the tabs 736 of the electrode assembly 730 to connect to wiring 770. Specifically, internal electrical wiring 772 starts from pogo pins 774 and extends through the top of sleeve 722, into wall 714 and through tab 736. The wiring 770 and internal electrical wiring 772 enable electrical connection of electrode 733 to the overall headset, despite the electrode 733 being removable and electrode assembly 730 being repositionable and adjustable in orientation within the headset.

Figure 7D:
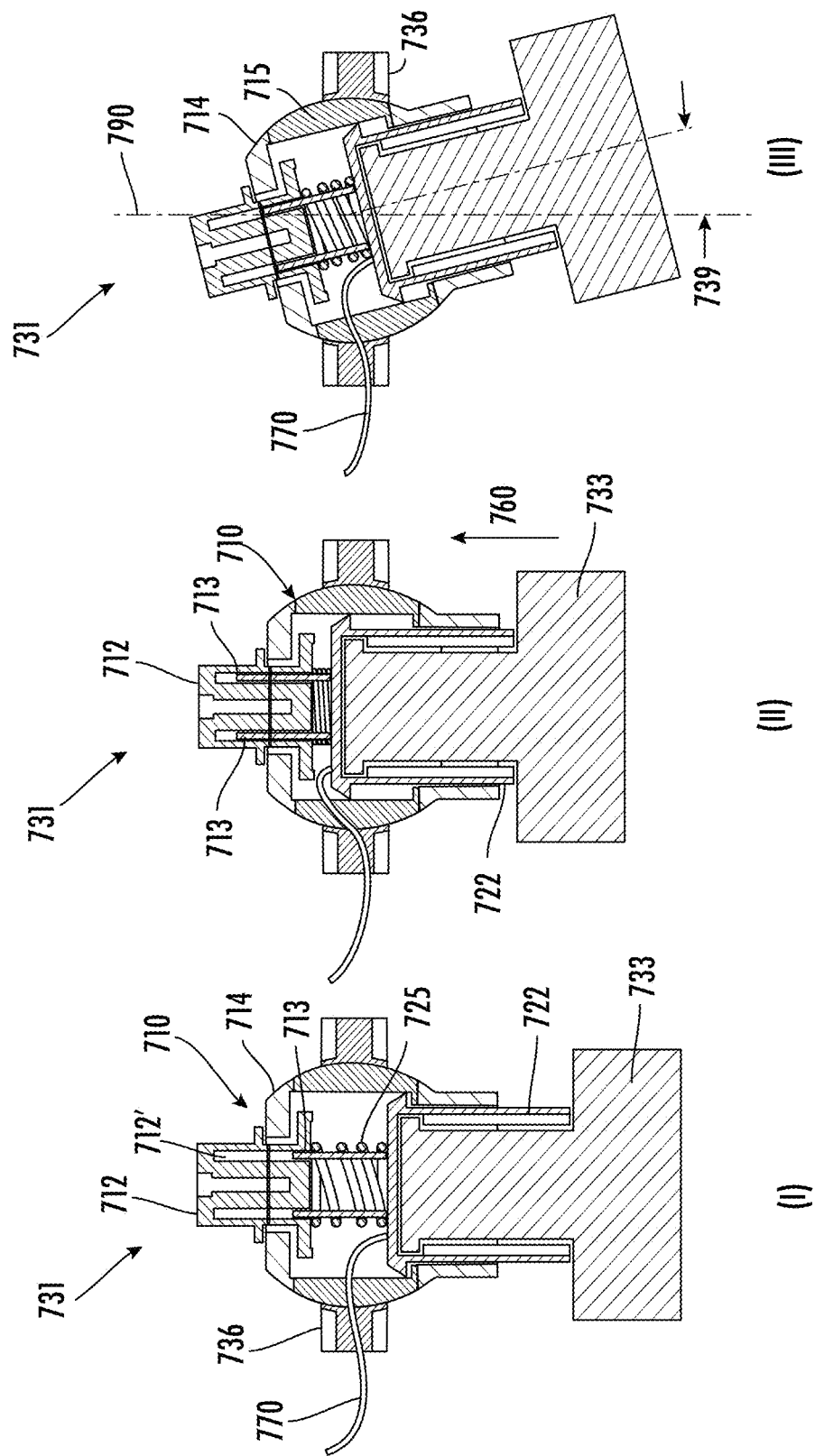
FIG. 7D shows cross-sectional views of wiring in a further embodiment of an electrode assembly, in accordance with some embodiments.

FIG. 7D shows another embodiment of an electrode assembly 731 and its wiring 770. In FIG. 7D, wiring 770 extends through tab 736 and connects to internal wiring in sleeve 722. The internal wiring is not shown in FIG. 7D for clarity but may be configured similar to internal electrical wiring 772 of FIG. 7C. The electrode assembly 731 includes a plunger 713 inside and parallel to elastic element 725. Elastic element 725 is illustrated as a coil spring in this embodiment but may take other forms such as an elastomeric piece as described in FIGS. 4C-4D. Plunger 713 may be, for example, multiple individual posts or a hollow cylinder. Plunger 713 slides into internal slots 712' of knob 712 when the sleeve 722 and electrode 733 are retracted (arrow 760) into the shell 710, as shown in state (II) compared to state (I). In electrode assembly 731, the outer geometry of walls 714 of the shell 710 is spherical in this embodiment, serving as a ball joint to provide omnidirectional rotation within tabs 736 (and consequently the arms of the overall headset). Tabs 736 have an inner curvature to receive the spherical shape of walls 714. That is, the tabs 736 protrude from opposite sides of an outer surface of the shell, and the outer surface of the shell 710 is spherical to provide multi-directional rotation within the tabs 736. State (III) shows the electrode assembly 731 having a tilt angle 739 with respect to the Z-axis 790, which is perpendicular to the tabs 736. The Z-axis 790 is consequently perpendicular to the headset arm (not shown in this figure) when mounted into the overall EEG headset. In this embodiment, the entire electrode assembly 731 except for tabs 736 rotate, where the tabs 736 remain stationary within the rails of the headset. The through-holes 715 in the walls 715 are large enough to enable the electrode assembly 731 to rotate without impeding (i.e., pinching or snagging) the wiring 770 through the tabs 736.

Figure 8:
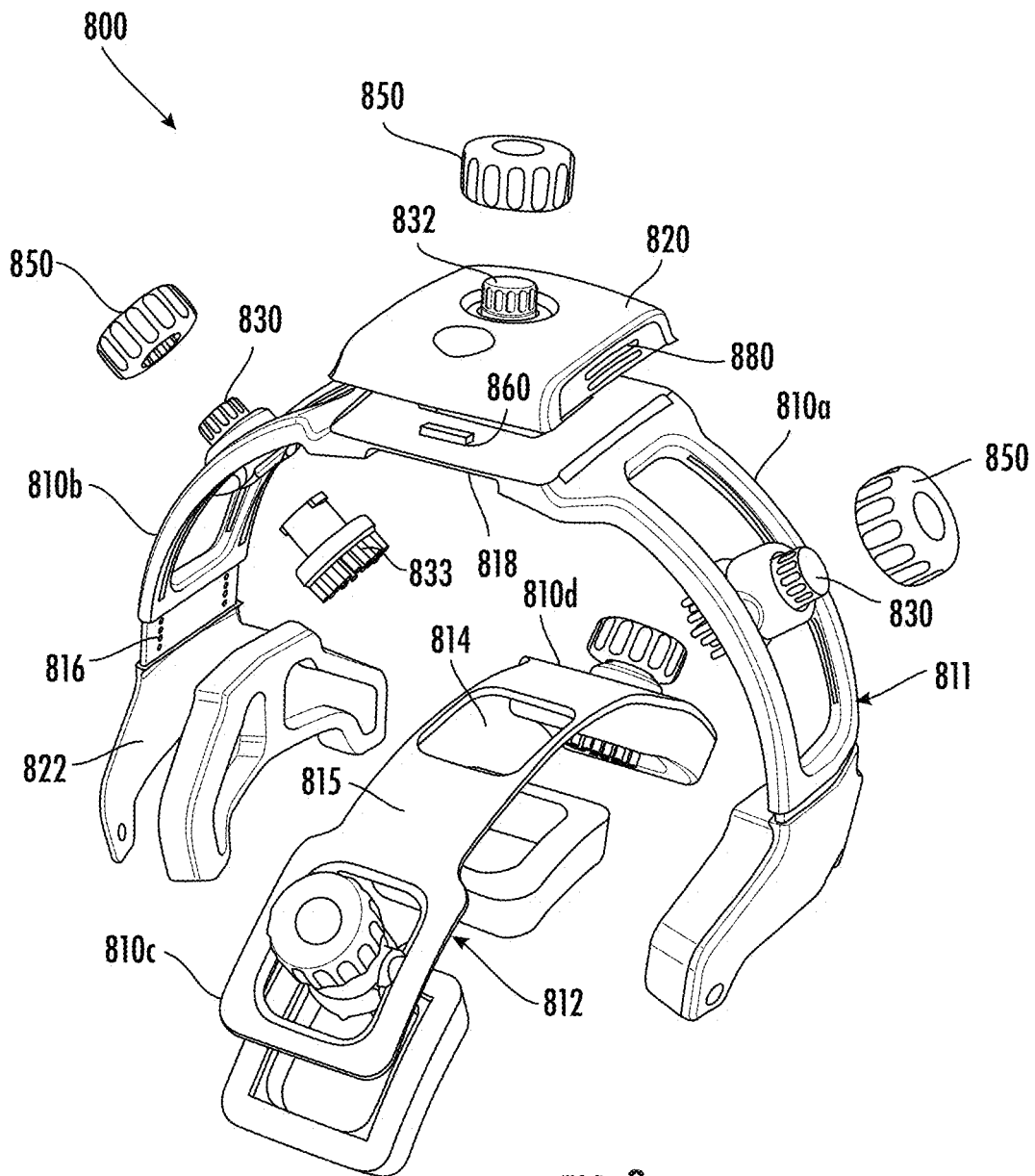
FIG. 8 is an exploded view of an EEG headset, in accordance with some embodiments.

FIG. 8 is an exploded view demonstrating the modular construction of headset 800, in accordance with some embodiments. Housing 820 contains electronics for electrodes of the headset 800 (or other operating circuitry and energy sources as required for the type of sensors being used in the headset) and is a separate component from the arms 810a-d, thus beneficially allowing different types of arms to be utilized with the housing 820. That is, arms 810a-d are detachable from housing 820 and may be interchanged with different types of arms. In the embodiment shown, arms 810a and 810b are made of one piece forming a first headband 811. Arms 810c and 810d are made of another piece, forming a second headband 812 that intersects the headband 811 when mounted to the housing 820. In other embodiments, each arm may be an individual piece, such as arm 810a being one piece and 810b being a separate piece, each individually attachable to the housing 820. For example, a user (e.g., clinician or patient) may choose to utilize only arms 810a-b in a particular situation, or both arms 810a-b with arms 810c-d in another situation, or three arms 810a, 810b and 810c in a further situation. The arms 810a-d (and headbands 811, 812) are made with flexible, resilient material so that the arms can flex apart from each other while being placed onto a person's head, but also spring back toward the person's head when the headset 800 has been fully donned. In other embodiments, additional elements may be included into the headset arms to provide spring-back toward the person's head, such as spring-loaded hinges or other mechanisms. Also shown in FIG. 8 are an electrode 833, which is replaceable by the user with one-handed abilities, and an accessory knob 850 to assist users that have limited dexterity in rotating the electrode assembly 830.

In the embodiment of FIG. 8, the arms 810a-b are illustrated as being perpendicular to the arms 810c-d, with housing 820 having a square shape to accommodate the orthogonal arrangement. For example, arms 810a-b are oriented laterally on a patient, extending from a first lateral edge and a second lateral edge of the housing 820, and arms 810c-d are in an anterior-to-posterior direction. In other embodiments, the arms may be oriented at other angles around the head, with the housing being configured accordingly. For example, housing 820 may have a hexagonal shape for six arms extending from the housing instead of four as shown in FIG. 8. In other embodiments, the housing shape can be independent of the arrangement of arms, such as having a circular shape.

The arms 810a-d are coupled to a bottom surface of the housing 820 while allowing electrode 832 of housing 820 to access the subject's head, such as through opening 814 in headband 812. The arms 810a-d are removably attached to a bottom surface of the housing 820 with mechanisms such as snap fits, latches, quick release mechanisms, or other fastening elements that can be performed with one limb and hand. For example, the connector 860 of headband 811 is illustrated as a tab that fits into a corresponding recess (not shown) in the bottom surface of the housing 820. Connector 860 can also be configured to electrically couple an electrode assembly that is mounted in the arms 810a-b to the electronic circuitry in the housing 820, by having wiring and/or electrical contacts that connect with the wiring 770 of FIGS. 7A-7C. Headband 812 has a bridge area 815 that fits into a recessed area 818 of headband 811. In some embodiments, the recessed area 818 may serve as a guide rail such that headband 812 can slide within the recessed area 818 to allow adjustability of the position of headband 812 on the subject's head. For example, headband 812 can slide anteriorly and posteriorly as indicated by arrow 162 of FIG. 1B.

Also shown in FIG. 8 are holes 816 in a portion of arm 810b that slides into a distal plate 822 of arm 810b. The holes 816 illustrate an embodiment for setting a desired length of arm 810b, where the holes 816 engage with a mating feature in distal plate 822. For example, distal 822 may contain spring-loaded balls that seat into holes 816 when the arm 810b is telescoped in and out of distal plate 822.

Figure 9A:
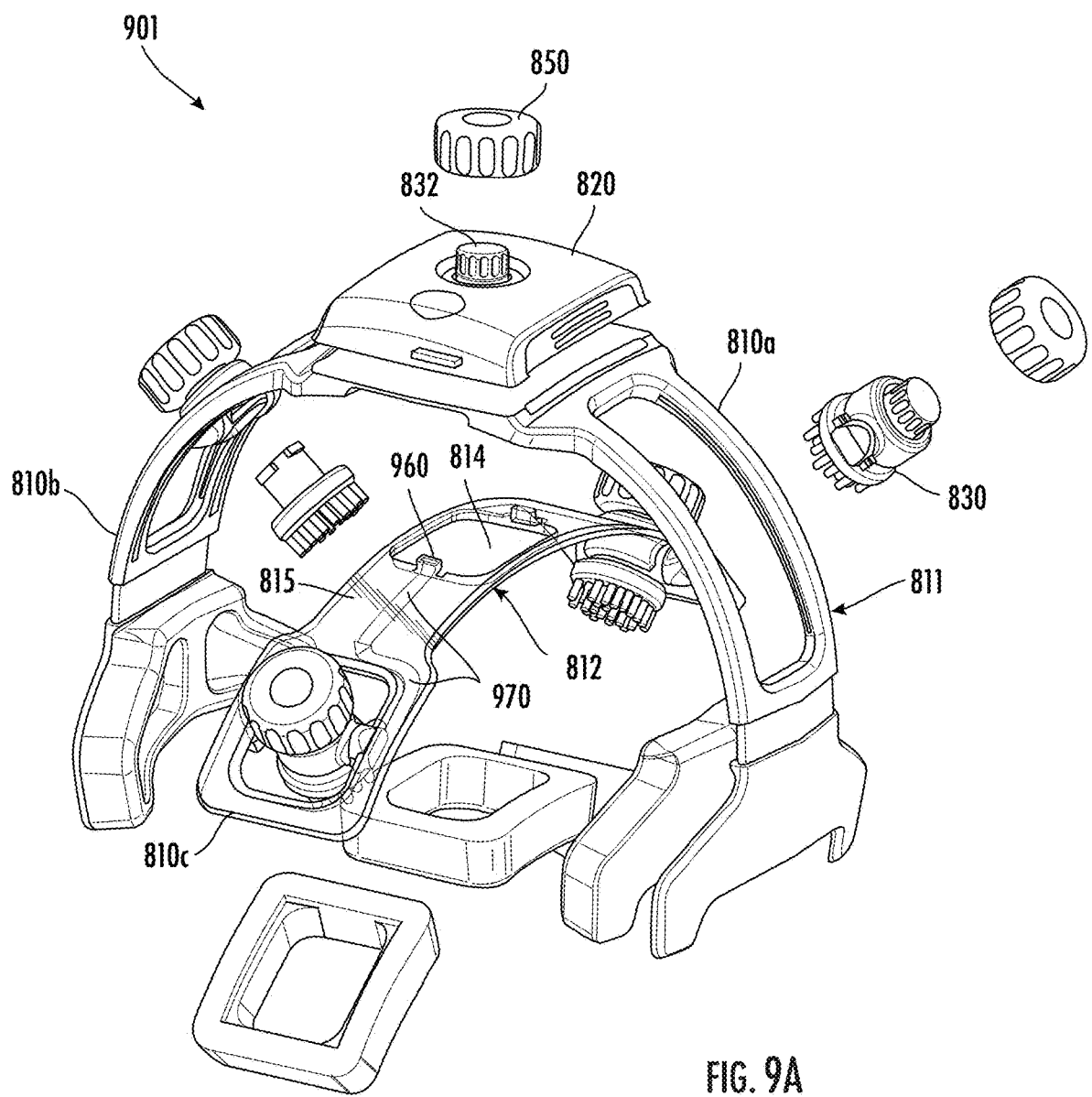
FIGS. 9A and 9B are exploded views illustrating electrical connections between modular components, in accordance with some embodiments.
Figure 9B:
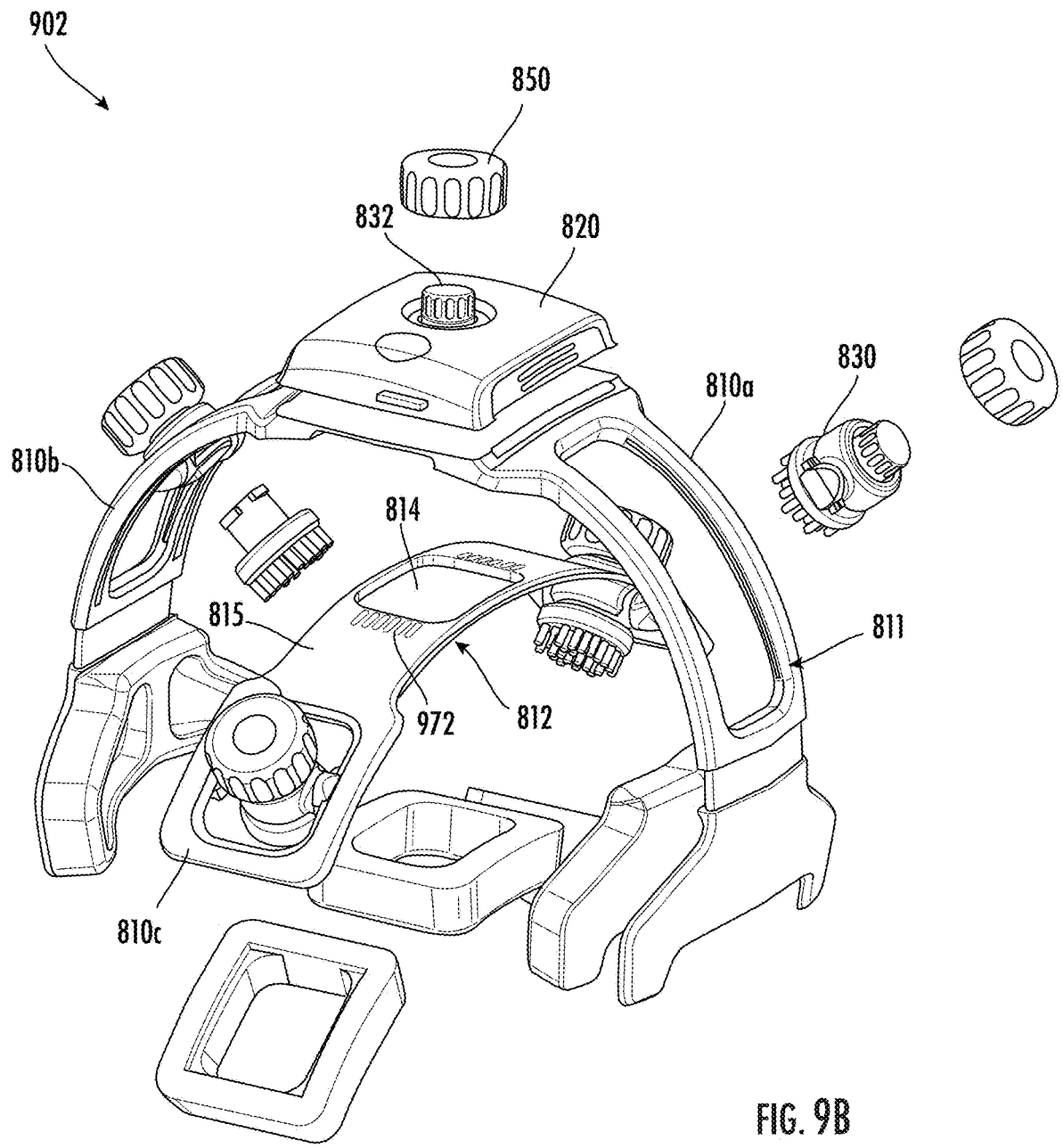

FIGS. 9A and 9B are exploded views of headsets 901 and 902 respectively, showing further embodiments of electrical connections of the modular components. The description of components from FIG. 8 that have the same reference numerals as in FIGS. 9A and 9B shall apply to headsets 901 and 902. In FIG. 9A, headband 812 has internal wiring 970 that runs along the sides (i.e., rails 716 of FIG. 7C) of arm 810c, through the bridge area 815 and to a connector 960, such as a ribbon cable connector. The wiring 970 may be cabling or ribbon cables, depending on shielding requirements, that run through a hollow interior of bridge area 815. In one embodiment, the connector 960 plugs into the intervening headband 811, where the headband 811 then electrically connects with the housing 820. In another embodiment, headband 811 may have an opening (not visible in this figure) that allows connector 960 to pass through the headband 811, such that the connector 960 plugs directly into the electronics module of housing 820. Connector 960 is located at the edge of opening 814 in this embodiment, but may be located elsewhere on the bridge 815 as long as it is connectable to the headband 811 or housing 820, depending on the configuration. In some embodiments, the wiring 970 (e.g., a ribbon cable) may include a strain relief and extra internal length/slack to accommodate a forward/back adjustability of the headband 812, such as headband 812 sliding crosswise with respect to the headband 811 and housing 820.

Headset 902 of FIG. 9B has similar internal wiring 970 (not shown in FIG. 9B) as headset 901, but instead of connector 960, headset 902 has contact pads 972 that are located on the surface of the bridge 815. Contact pads 972 are located at the edge of opening 814 in this embodiment, but may be located elsewhere on the bridge 815 as long as they are connectable to the headband 811 or housing 820, as needed. The corresponding connection areas on the housing 820 or headband 811 may be configured with, for example, pogo/spring loaded pins that make contact with contact pads 972. Contact pads 972 may be configured for point contact, such as circles with a similar diameter as their mating pogo pins, or contact pads 972 may be elongated as shown in FIG. 9B. The oblong shape of contact pads 972 in FIG. 9B enables electrical contact to be maintained when the headband 812 is slid forward or backward with respect to the headband 811 and housing 820.

Figure 10A:
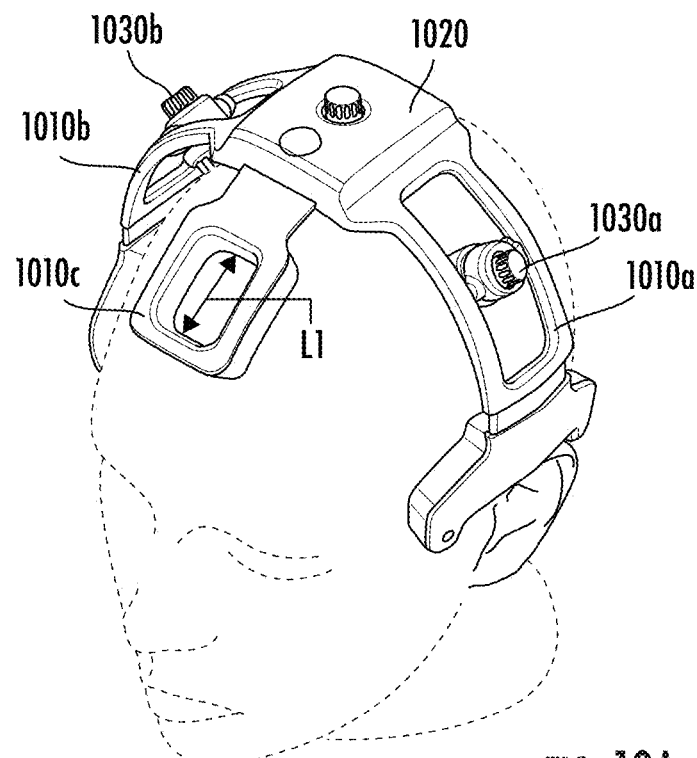
FIGS. 10A-10D are isometric views of modular configurations of EEG headsets, in accordance with some embodiments.
Figure 10B:
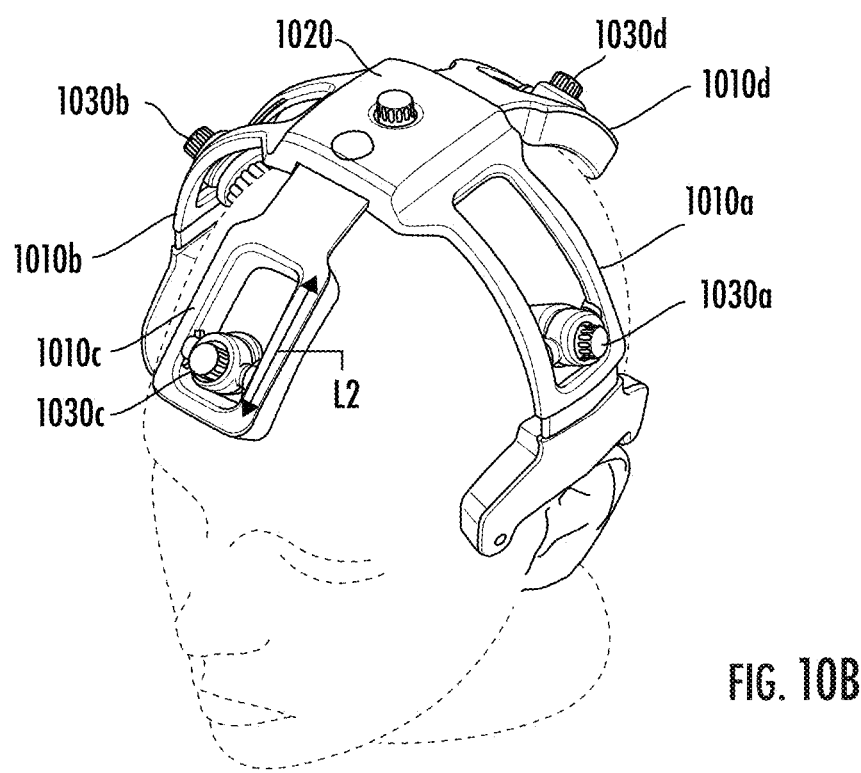
Figure 10C:
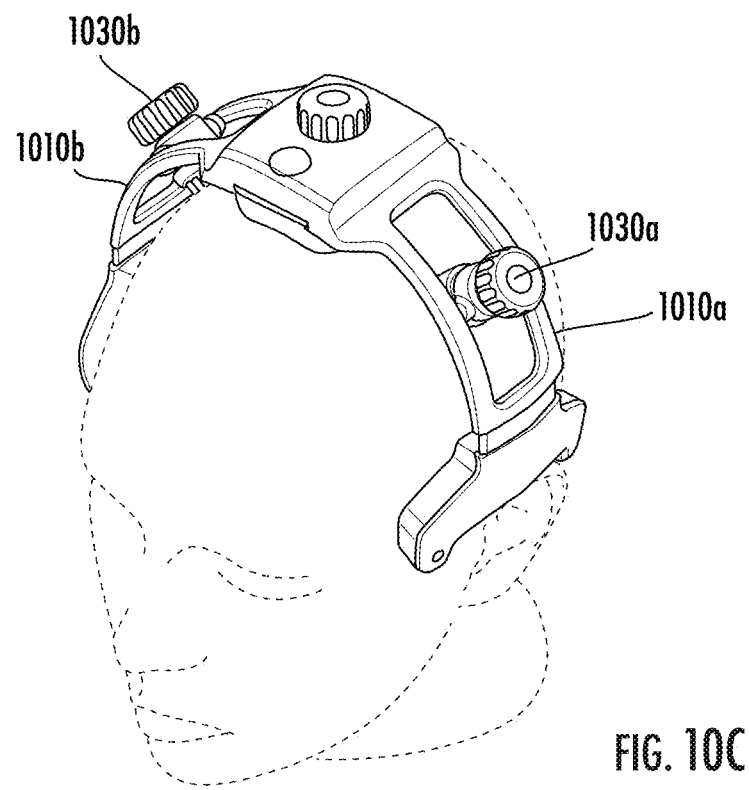
Figure 10D:
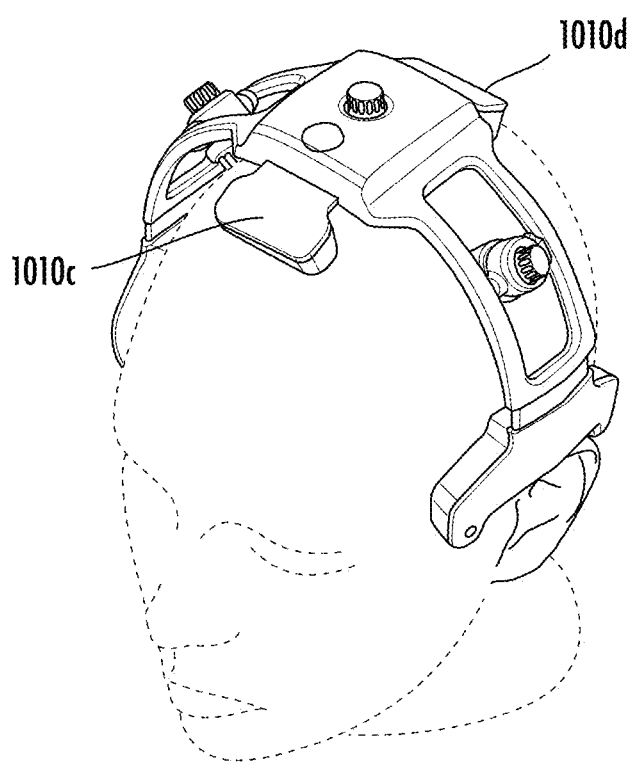

FIGS. 10A-10D show various headset configurations that are possible due to the modular construction of the housing with detachable arms. FIG. 10A shows an embodiment with three arms 1010a, 1010b and 1010c removably attached to a housing 1020. First arm 1010a has an electrode assembly 1030a, and second arm 1010b has an electrode assembly 1030b. Third arm 1010c has no electrode assembly but serves to help stabilize the headset when seated on a subject's head. FIG. 10B shows an embodiment having four arms 1010a-d removably coupled to housing 1020, with four electrode assemblies 1030a-d. Length L2 of the aperture in arm 1010c is longer than length L1 of the aperture in arm 1010c in FIG. 10A, such as for a person with a larger head or needing an electrode placed further down on the forehead than other people. Also shown in FIG. 10B are electrode assemblies 1030a and 1030c being positioned distally on the arms 1010a and 1010c, rather than centrally along the lengths of the arms as in other embodiments (e.g., FIG. 10A). FIG. 10C shows an embodiment in which only lateral arms 1010a and 1010b are used, without crosswise arms (e.g., anterior-posterior arms). In FIG. 10D, anterior-to-posterior arms 1010c and 1010d have no apertures for arms, only plates that help stabilize the headset on a subject's head. In summary, FIGS. 10A-10D illustrate examples of various arm and electrode configurations that are possible with the modular design of a housing that contains the electronics and is detachable from headset arms.

Figure 11:
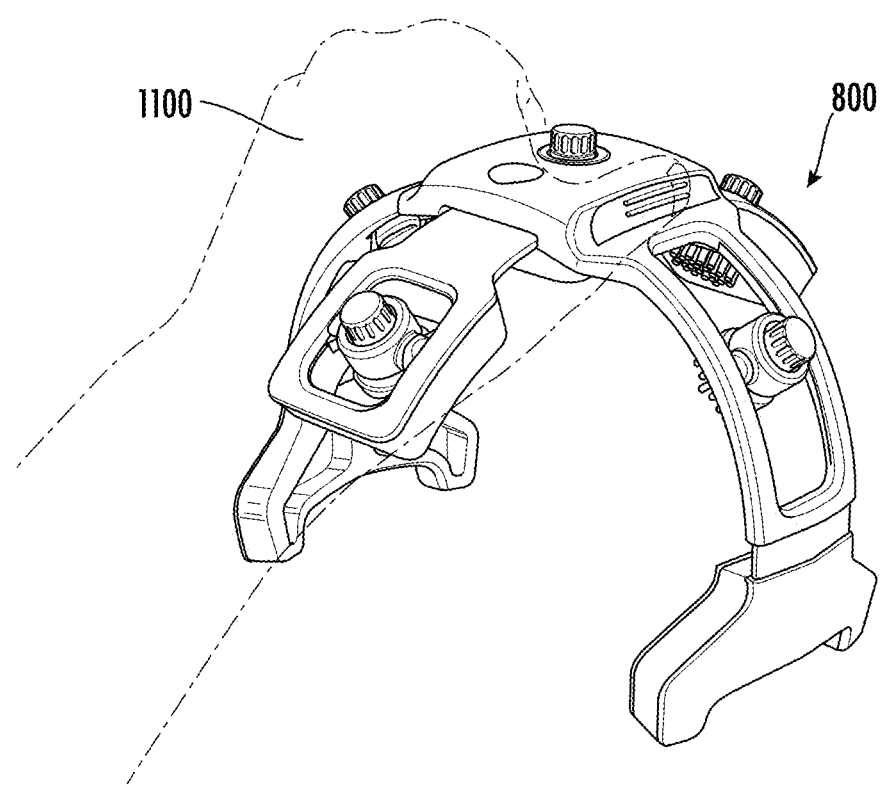
FIG. 11 is a perspective view demonstrating one-handed donning of an EEG headset, in accordance with some embodiments.

Returning to FIG. 8, the headset 800 includes grip elements 880 on housing 820, which are raised features embodied as linear, horizontal bars in this embodiment, but may be configured in other geometries such as dots or curvilinear shapes, or may be recessed features. Grip elements 880 are shown on a lateral edge (facing the lateral sides of the patient's head) of housing 820 in this embodiment. In some embodiments, grip elements 880 may be on multiple edges of the housing 820, such as one or more of an anterior edge (facing the subject's forehead), a posterior edge (facing the back of the subject's head), and a lateral edge. The grip elements 880 enable the headset to be donned one-handed as shown in FIG. 11, where a person's hand 1100 can lift the assembled headset 800 by holding grip elements 880.

Figure 12:
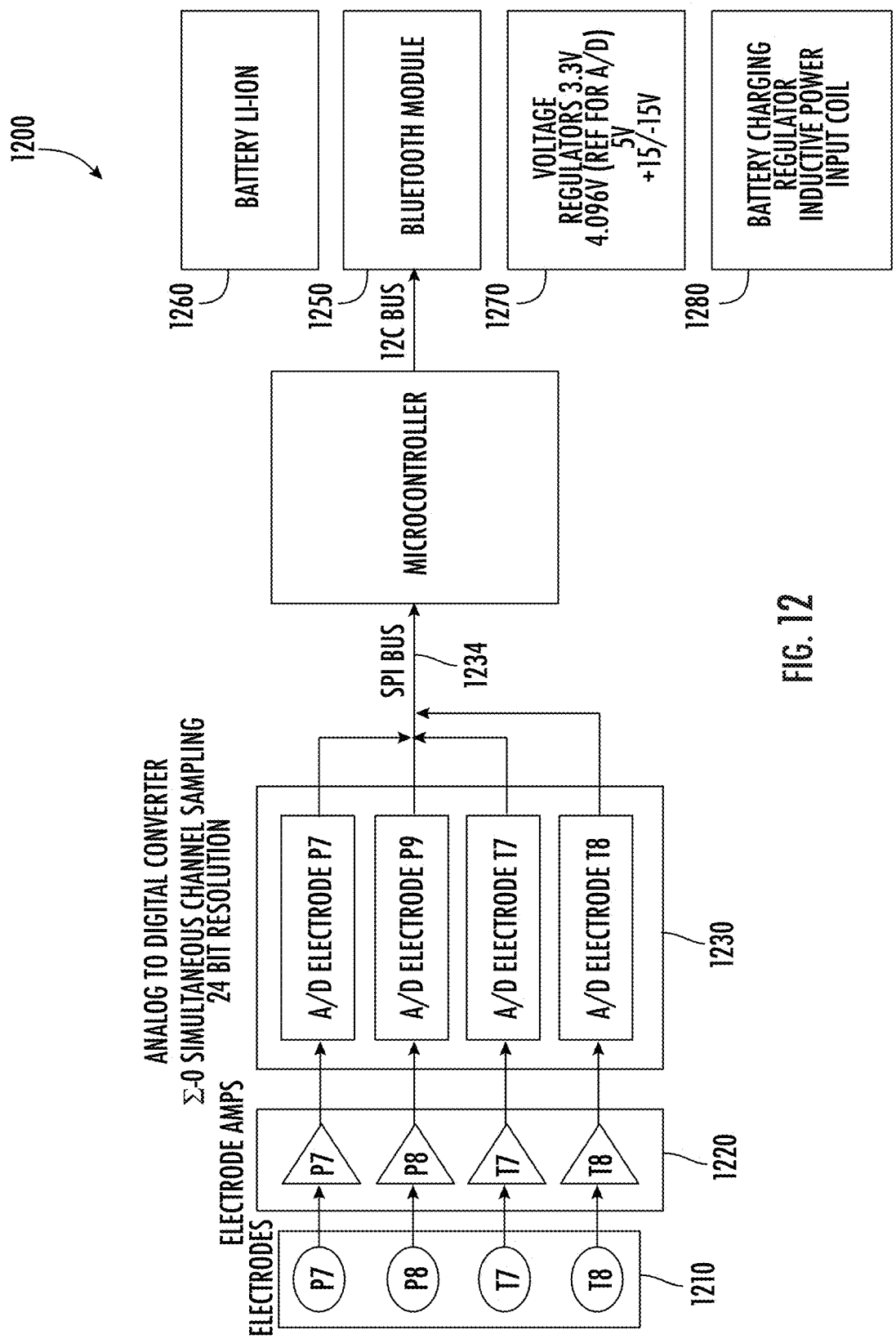
FIG. 12 is schematic of example electronics that can be used in conjunction with EEG headsets, in accordance with some embodiments.

FIG. 12 is a schematic diagram of electronics 1200 that can be included in the housings of the headsets of the present disclosure (e.g., housing 820 of FIG. 8 or housing 1020 of FIG. 10A). The housing serves as an electronics module, containing various electronic components. FIG. 12 is embodied for an EEG electrode; however, in other embodiments the housing can contain one or more energy sources and operational components for other types of sensors such as electromagnetic, infrared or near-infrared sensors, or other sensors for other wavelengths of light. As shown, the electronics 1200 includes amplifier circuitry 1220 to amplify the signal recorded at the electrodes, and analog-to-digital (A/D) converter circuitry 1230 to digitize the amplified sensed analog signal. The electronics 1200 also includes controller circuitry (a microcontroller 1240 as shown) which provides the glue logic between the A/D output and wireless transmitter circuitry 1250, packaging up the data received from the A/D conversion circuitry 1230, providing that packaged data to the wireless transmitter circuitry 1250 or module (which in this example is a BLUETOOTH® module), and controlling the wireless transmitter circuitry. The packaging of data includes assembling the A/D output into a format for a data transmission or messaging protocol, which in the example above is a Bluetooth protocol. The electronics 1200 also includes a battery 1260 or other power source, voltage regulators 1270, and a battery charging regulator 1280. A power source such as the battery 1260 shown is needed for the transmitter circuitry 1250, microcontroller 1240 and other circuitry, as well as the circuitry provided at the left side of FIG. 12. One example of a battery is a cell phone battery, but other battery power sources may be applicable.

In some embodiments, the initial amplification circuitry 1220 and A/D conversion circuitry 1230 may be provided with the electrodes 1210 of the EEG headset, and specifically on a circuit board provided with that electrode assembly which may be, for example, the electrode assembly 830 of FIG. 8. In one embodiment, the housing (e.g., housing 820 of FIG. 8) includes all of the components shown in the right-hand portion of FIG. 12, namely, the microcontroller 1240, the battery 1260, transmission module (transmitter circuitry 1250), and regulator circuitry (voltage regulator 1270 and battery charging regulator 1280). Alternatively, the microcontroller 1240 may be provided with the electrode assembly, and not in the housing. In the embodiment shown in FIG. 12, there is provided a serial peripheral interface (SPI) 1234 from the output of the A/D converter 1230, to multiplex the digitized data onto one serial channel. As is known, the bus connection may include more than one line, for example to provide a chip select function. In other words, in this embodiment the interconnection does not require a separate wire for each channel. In addition, the A/D conversion circuitry 1230 may be a multi-channel A/D converter which does not provide separate output channels. In addition to the electronics 1200, there may be provided an on/off switch for the user to activate, along with a light provided at the front of the housing or elsewhere on the headset (which the user may see for example in a mirror) enabling the user to confirm that the headset power is activated or not.

In various embodiments, electronic components in the housings can include, but not are limited to, the following: one or more batteries, microprocessor(s), one or more types of memory devices, control circuitry, transceivers, antennae, gyroscopes, accelerometers, oximetry circuitry, electrode amplifiers, various kinds of connectors (e.g., USB ports, power supply ports, audio/video input and/or output ports, network connection ports, etc.), user interface elements (e.g., a graphical display, a touchscreen graphical display, a microphone to receive audio input from the user, a camera, audio speakers, indicator lights, buttons, keys, switches, tactile feedback devices, and the like). The one or more batteries can allow the EEG headset to be portable; that is, the batteries can provide power to the electrodes of the EEG headset, and may be recharged via an adapter or charging device. In some embodiments, the batteries of the EEG headset can be inductively recharged.

The brain sensing headset (e.g., EEG headset) includes the processing and controller circuitry to operate the EEG headset in training modes, operational modes (e.g., rehabilitation sessions), calibration modes, communications modes, and so on. As such, the EEG headset can include one or more central processing units, volatile memory such as random access memory (RAM), and non-volatile memory such as read-only memory (ROM) and/or various forms of programmable read-only memory (PROM) for the storage of software or firmware programs and operating parameters that may be periodically updated. In terms of software and/or firmware programs, the EEG headset may include various programs that are stored in non-volatile memory that include executable program instructions that are executed by the processing and control circuitry to carry out the various processing functions. The non-volatile memory may also include information storage areas for operational parameter settings or other input information used during the operation of the EEG headset. The settings and other input information may be input by a user (or clinician), or may be transmitted to the EEG headset from a remote system.

The electrodes of the electrode assembly may operate in a passive mode or in an active mode. Operation in an active mode means some circuitry, typically an amplifier, is co-located with the electrode, with power provided to that amplifier circuitry, so that a signal is provided on a transmission line that is less vulnerable to noise. The sooner the sensed signal is amplified, a low impedance path will be produced that may negate most noise sources. In an active mode, operation amplification characteristics may be important in BCI applications, particularly if low intensity brain signals like an ipsilateral signal is being acquired and used. In a passive mode, the sensor sends a relatively weak electrical signal over a transmission line. To the extent the system may be able to be designed to operate in a passive mode and not have noise interfere with the system operation, doing so may be desirable for cost reasons. Passive electrodes are typically less expensive to fabricate or purchase than active electrodes (for example, perhaps one tenth the cost), and using a passive electrode design may provide more flexibility in the design in that electronics provided in a co-located fashion with the electrode are not necessary.

Embodiments of brain sensing headsets disclosed herein advantageously enable a person to consistently place sensors (e.g., electrodes) at the targeted locations, with reliable contact with the subject's scalp contact due to the multi-directional adjustability of the uniquely designed sensor assemblies. The donning of the headsets as well as replacement of sensors, when required, may all be performed with one hand and arm, which is particularly beneficial to stroke patients who may have an impaired limb with limited use. Furthermore, the brain sensing headsets of the present disclosure are modular, having a housing that serves as an electronics module and interchangeable arms that allow the number and locations of sensors to be customized.

In embodiments, devices for recording brain activity of a subject include a first arm (e.g., arm 110*a* of FIG. 1A) shaped to extend along a subject's head, the first arm having a first pair of rails (e.g., rails 116 of FIG. 2A) along a length of the first arm. The first pair of rails borders a first aperture (e.g., aperture 114 of FIG. 2A) that allows access to the subject's head, and the first pair of rails has grooves (e.g., grooves 717 of FIG. 7A) along interior edges facing the first aperture. The device includes an electrode assembly (e.g., electrode assembly 130 of FIG. 1A, electrode assembly 300 of FIG. 4A) that has multi-directional adjustability in orientation. The electrode assembly includes a shell with tabs (e.g., shell 310, tabs 316 of FIG. 4A) protruding from opposite sides of an outer surface of the shell, the tabs being rotatable with respect to the shell; a sleeve (e.g., sleeve 320) inside the shell, the sleeve having a clearance (e.g., clearance 328) between the sleeve and the shell to allow angular tilting of the sleeve within the shell; an elastic element (e.g., elastic element 325) attaching a first end of the sleeve to an interior end of the shell; and an electroencephalography (EEG) electrode (e.g., electrode 330) removably inserted into the sleeve, with a contact surface of the EEG electrode facing the subject's head. The electrode assembly is mounted in the first arm, with the tabs slidably seated in the grooves of the first pair of rails. The device also includes a housing (e.g., housing 120 of FIG. 1A) having a bottom surface facing the subject's head, where the housing contains an energy source and electronic circuitry (e.g., FIG. 12) for the electrode assembly; and a second arm (e.g., arm 110*b*, 110*c* or 110*d*) removably coupled to the housing, the second arm extending along the subject's head. The first arm is removably coupled to the housing and extends along the subject's head in a direction different than the second arm.

In some embodiments, the device includes a fixed electrode (e.g., electrode 132 of FIG. 1A) mounted to the housing. In some embodiments, the second arm has a second pair of rails along a second length of the second arm, the second pair of rails bordering a second aperture that allows access to the subject's head, the second pair of rails having second grooves along interior edges facing the second aperture; and the device further comprises a plurality of the electrode assemblies, where one electrode assembly of the plurality of the electrode assemblies is mounted in the second arm, with the tabs slidably seated in the second grooves of the second pair of rails. In some embodiments, the second arm further comprises a connector (e.g., connector 860, 960) that removably couples the second arm to the bottom surface of the housing; and the connector electrically couples the one electrode assembly that is mounted in the second arm to the electronic circuitry in the housing. In some embodiments, a compressible pad (e.g., pad 140*c*, 140*d*) surrounds the second aperture on an underside of the second arm, facing the subject's head, where the compressible pad comprises an electromagnetic interference (EMI) shield. In some embodiments, the second arm has a compressible pad (e.g., pad 140*a*, 140*b*, 140*c*, 140*d*) facing the subject's head.

In some embodiments, the elastic element (e.g., elastic element 325, 625) comprises a first spring force; and the device further comprises a compressible pad (e.g., pad 140*c*, 140*d*, 640) mounted to the first arm and facing the subject's head, the compressible pad having a second spring force that is less than the first spring force. In some embodiments, the shell has a Z-axis (e.g., Z-axis 390, FIG. 4A) perpendicular to the subject's head; the elastic element enables movement of the EEG electrode along the Z-axis; the angular tilting (e.g., angle 339, FIG. 4A) of the sleeve within the shell is with respect to the Z-axis; and the tabs enable the EEG electrode to rotate about a Y-axis perpendicular to the Z-axis. In some embodiments, the electrode assembly further comprises electrical wiring (e.g., internal electrical wiring 772, FIG. 7C) from the sleeve to one of the tabs. In some embodiments, the clearance (e.g., clearance 328, FIG. 4A) enables up to 20° of the angular tilting. In some embodiments, the EEG electrode is removably inserted into the sleeve with a turn-locking mechanism (e.g., FIGS. 5A-5B), the EEG electrode comprising a cylindrical body having a protrusion that mates with a recess in an interior of the sleeve. In some embodiments, the housing further comprises a grip element (e.g., grip elements 880) on an edge of the housing, the edge being at least one of an anterior edge, a posterior edge, or a lateral edge (e.g., on a first lateral edge or a second lateral edge).

In embodiments, a device for recording brain activity of a subject includes a plurality of electrode assemblies (e.g., electrode assembly 130 of FIG. 1A, electrode assembly 300 of FIG. 4A). Each electrode assembly has multi-directional adjustability in orientation and includes: a shell with tabs protruding from opposite sides of an outer surface of the shell, the tabs being rotatable with respect to the shell; a sleeve inside the shell, the sleeve having a clearance between the sleeve and the shell to allow angular tilting of the sleeve within the shell; an elastic element attaching a first end of the sleeve to an interior end of the shell; and an electroencephalography (EEG) electrode removably inserted into the sleeve, with a contact surface of the EEG electrode facing a subject's head. The device also includes a housing (e.g., housing 120 of FIG. 1A) having a bottom surface, a first lateral edge, and a second lateral edge, wherein the housing contains an energy source and electronic circuitry (e.g., FIG. 12) for the plurality of electrode assemblies. A first arm (e.g., arm 110*a* of FIG. 1A or arm 1010*a* of FIGS. 10A-10D) is removably coupled to the housing and shaped to extend along the subject's head from the first lateral edge of the housing, the first arm having a first pair of rails along a first length of the first arm. The first pair of rails borders a first aperture that allows access to the subject's head, and the first pair of rails has first grooves along interior edges facing the first aperture. A second arm (e.g., arm 110*b* of FIG. 1A or arm 1010*b* of FIGS. 10A-10D) is removably coupled to the housing and is shaped to extend along the subject's head from the second lateral edge of the housing. The second arm has a second pair of rails along a second length of the second arm, wherein the second pair of rails borders a second aperture that allows access to the subject's head. The second pair of rails has second grooves along interior edges facing the second aperture. A third arm (e.g., arm 110*c* or 110*d* of FIG. 1A, or arm 1010*c* or 1010*d* of FIGS. 10A-10D) is removably coupled to the housing, the third arm extending along the subject's head in an anterior-to-posterior direction. A first electrode assembly of the plurality of electrode assemblies is mounted in the first aperture of the first arm, the tabs of the first electrode assembly being slidably seated in the first grooves of the first aperture. A second electrode assembly of the plurality of electrode assemblies is mounted in the second aperture of the second arm, the tabs of the second electrode assembly being slidably seated in the second grooves of the second aperture.

In some embodiments, the third arm has a third pair of rails along a third length of the third arm, wherein the third pair of rails borders a third aperture that allows access to the subject's head, and the third pair of rails has third grooves along interior edges facing the third aperture. A third electrode assembly of the plurality of electrode assemblies is mounted in the third arm, with the tabs of the third electrode assembly slidably seated in the third grooves of the third aperture. In some embodiments, the third arm further comprises a connector that removably couples the third arm to the bottom surface of the housing; and the connector electrically couples the third electrode assembly to the electronic circuitry in the housing. In some embodiments, the device further includes a compressible pad that surrounds the third aperture on an underside of the third arm, facing the subject's head; and the compressible pad comprises an electromagnetic interference (EMI) shield.

In some embodiments, the third arm has a compressible pad facing the subject's head. In some embodiments, the elastic element comprises a first spring force; and the first arm and the second arm each comprise a compressible pad facing the subject's head, the compressible pad having a second spring force that is less than the first spring force.

In some embodiments, devices for recording brain activity of a subject include a first arm shaped to extend along a subject's head, the first arm having a first aperture that allows access to the subject's head. A sensor assembly of the device has multi-directional adjustability in orientation. The sensor assembly includes a shell configured for multi-directional rotation; a sleeve inside the shell; an elastic element attaching a first end of the sleeve to an interior end of the shell; and a sensor removably inserted into the sleeve, with a contact surface of the sensor facing the subject's head. The device also includes a housing that contains an energy source and operational components for the sensor assembly.

In some embodiments, devices can include a second arm removably coupled to the housing, the second arm extending along the subject's head, where the first arm is removably coupled to the housing and extends along the subject's head in a direction different than the second arm. In some embodiments, the sensor is an electroencephalography (EEG) electrode. In some embodiments, the sensor is a light sensor, such as a near-infrared sensor.

In some embodiments, the shell has tabs protruding from opposite sides of an outer surface of the shell; and the outer surface of the shell is spherical to provide the multi-directional rotation within the tabs. In some embodiments, the first arm has a first pair of rails along a first length of the first arm, the first pair of rails bordering the first aperture and having grooves along interior edges facing the first aperture; the shell has tabs protruding from opposite sides of an outer surface of the shell, the tabs being rotatable with respect to the shell; the sleeve has a clearance between the sleeve and the shell to allow angular tilting of the sleeve within the shell; and the sensor assembly is mounted in the first arm, with the tabs slidably seated in the grooves of the first pair of rails.

In some embodiments, the elastic element comprises a first spring force; and the device further comprises a compressible pad mounted to the first arm and facing the subject's head, the compressible pad having a second spring force that is less than the first spring force. In some embodiments, the shell has a Z-axis perpendicular to the subject's head; the elastic element enables movement of the sensor along the Z-axis; and the multi-directional rotation comprises angular tilting with respect to the Z-axis and rotation about a Y-axis perpendicular to the Z-axis. In some embodiments, the sensor is removably inserted into the sleeve with a turn-locking mechanism, the sensor comprising a cylindrical body having a protrusion that mates with a recess in an interior of the sleeve.

Reference has been made in detail to embodiments of the disclosed invention, one or more examples of which been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A device for recording brain activity of a subject, comprising:
   i) a first arm shaped to extend along a subject's head, the first arm having a first pair of rails along a first length of the first arm, wherein the first pair of rails borders a first aperture that allows access to the subject's head, and the first pair of rails has grooves along interior edges facing the first aperture;
   ii) an electrode assembly that has multi-directional adjustability in orientation, the electrode assembly comprising:
      a shell with tabs protruding from opposite sides of an outer surface of the shell, the tabs being rotatable with respect to the shell;
      a sleeve inside the shell, the sleeve having a clearance between the sleeve and the shell to allow angular tilting of the sleeve within the shell;
      an elastic element attaching a first end of the sleeve to an interior end of the shell; and
      an electroencephalography (EEG) electrode removably inserted into the sleeve, with a contact surface of the EEG electrode facing the subject's head;
      wherein the electrode assembly is mounted in the first arm, with the tabs slidably seated in the grooves of the first pair of rails;
   iii) a housing having a bottom surface facing the subject's head, wherein the housing contains an energy source and electronic circuitry for the electrode assembly; and
   iv) a second arm removably coupled to the housing, the second arm extending along the subject's head;
      wherein the first arm is removably coupled to the housing and extends along the subject's head in a direction different than the second arm.

2. The device of claim 1, further comprising a fixed electrode mounted to the housing.

3. The device of claim 1, wherein:
   the second arm has a second pair of rails along a second length of the second arm, the second pair of rails bordering a second aperture that allows access to the subject's head, the second pair of rails having second grooves along interior edges facing the second aperture; and
   the device further comprises a plurality of the electrode assemblies, one electrode assembly of the plurality of the electrode assemblies being mounted in the second arm, with the tabs slidably seated in the second grooves of the second pair of rails.

4. The device of claim 3, wherein:
the second arm further comprises a connector that removably couples the second arm to the bottom surface of the housing; and
the connector electrically couples the one electrode assembly that is mounted in the second arm to the electronic circuitry in the housing.

5. The device of claim 3, further comprising a compressible pad that surrounds the second aperture on an underside of the second arm, facing the subject's head; and
wherein the compressible pad comprises an electromagnetic interference (EMI) shield.

6. The device of claim 1, wherein the second arm has a compressible pad facing the subject's head.

7. The device of claim 1, wherein:
the elastic element comprises a first spring force; and
the device further comprises a compressible pad mounted to the first arm and facing the subject's head, the compressible pad having a second spring force that is less than the first spring force.

8. The device of claim 1, wherein:
the shell has a Z-axis perpendicular to the subject's head;
the elastic element enables movement of the EEG electrode along the Z-axis;
the angular tilting of the sleeve within the shell is with respect to the Z-axis; and
the tabs enable the EEG electrode to rotate about a Y-axis perpendicular to the Z-axis.

9. The device of claim 1, wherein the electrode assembly further comprises electrical wiring from the sleeve to one of the tabs.

10. The device of claim 1, wherein the clearance enables up to 20° of the angular tilting.

11. The device of claim 1, wherein the EEG electrode is removably inserted into the sleeve with a turn-locking mechanism, the EEG electrode comprising a cylindrical body having a protrusion that mates with a recess in an interior of the sleeve.

12. The device of claim 1, wherein the housing further comprises a grip element on an edge of the housing, the edge being at least one of an anterior edge, a posterior edge, or a lateral edge.

13. A device for recording brain activity of a subject, comprising:
i) a plurality of electrode assemblies, each electrode assembly having multi-directional adjustability in orientation and comprising:
a shell with tabs protruding from opposite sides of an outer surface of the shell, the tabs being rotatable with respect to the shell;
a sleeve inside the shell, the sleeve having a clearance between the sleeve and the shell to allow angular tilting of the sleeve within the shell;
an elastic element attaching a first end of the sleeve to an interior end of the shell; and
an electroencephalography (EEG) electrode removably inserted into the sleeve, with a contact surface of the EEG electrode facing a subject's head;
ii) a housing having a bottom surface, a first lateral edge, and a second lateral edge, wherein the housing contains an energy source and electronic circuitry for the plurality of electrode assemblies;
iii) a first arm removably coupled to the housing and shaped to extend along the subject's head from the first lateral edge of the housing, the first arm having a first pair of rails along a first length of the first arm, wherein the first pair of rails borders a first aperture that allows access to the subject's head, and the first pair of rails has first grooves along interior edges facing the first aperture;
iv) a second arm removably coupled to the housing and being shaped to extend along the subject's head from the second lateral edge of the housing, the second arm having a second pair of rails along a second length of the second arm, wherein the second pair of rails borders a second aperture that allows access to the subject's head, and the second pair of rails has second grooves along interior edges facing the second aperture; and
v) a third arm removably coupled to the housing, the third arm extending along the subject's head in an anterior-to-posterior direction;
wherein:
a first electrode assembly of the plurality of electrode assemblies is mounted in the first aperture of the first arm, the tabs of the first electrode assembly being slidably seated in the first grooves of the first aperture; and
a second electrode assembly of the plurality of electrode assemblies is mounted in the second aperture of the second arm, the tabs of the second electrode assembly being slidably seated in the second grooves of the second aperture.

14. The device of claim 13, wherein:
the third arm has a third pair of rails along a third length of the third arm, wherein the third pair of rails borders a third aperture that allows access to the subject's head, and the third pair of rails has third grooves along interior edges facing the third aperture; and
a third electrode assembly of the plurality of electrode assemblies is mounted in the third arm, with the tabs of the third electrode assembly slidably seated in the third grooves of the third aperture.

15. The device of claim 14, wherein:
the third arm further comprises a connector that removably couples the third arm to the bottom surface of the housing; and
the connector electrically couples the third electrode assembly to the electronic circuitry in the housing.

16. The device of claim 14, further comprising a compressible pad that surrounds the third aperture on an underside of the third arm, facing the subject's head; and
wherein the compressible pad comprises an electromagnetic interference (EMI) shield.

17. The device of claim 13, wherein the third arm has a compressible pad facing the subject's head.

18. The device of claim 13, wherein:
the elastic element comprises a first spring force; and
the first arm and the second arm each comprise a compressible pad facing the subject's head, the compressible pad having a second spring force that is less than the first spring force.

19. The device of claim 13, wherein:
the shell has a Z-axis perpendicular to the subject's head;
the elastic element enables movement of the EEG electrode along the Z-axis;
the angular tilting of the sleeve within the shell is with respect to the Z-axis; and
the tabs enable the EEG electrode to rotate about a Y-axis perpendicular to the Z-axis.

20. The device of claim 13, wherein the electrode assembly further comprises electrical wiring from the sleeve to one of the tabs.

21. The device of claim 13, wherein the clearance enables up to 20° of the angular tilting.

22. The device of claim 13, wherein the EEG electrode is removably inserted into the sleeve with a turn-locking mechanism, the EEG electrode comprising a cylindrical body having a protrusion that mates with a recess in an interior of the sleeve.

23. The device of claim 13, wherein the housing further comprises a grip element on the first lateral edge or the second lateral edge.

24. A device for recording brain activity of a subject, comprising:
   i) a first arm shaped to extend along a subject's head, the first arm having a first aperture that allows access to the subject's head;
   ii) a sensor assembly that has multi-directional adjustability in orientation, the sensor assembly comprising:
      a shell configured for multi-directional rotation;
      a sleeve inside the shell;
      an elastic element attaching a first end of the sleeve to an interior end of the shell; and
      a sensor removably inserted into the sleeve, with a contact surface of the sensor facing the subject's head; and
   iii) a housing that contains an energy source and operational components for the sensor assembly;
   wherein:
      the first arm has a first pair of rails along a first length of the first arm, the first pair of rails bordering the first aperture and having grooves along interior edges facing the first aperture;
      the shell has tabs protruding from opposite sides of an outer surface of the shell, the tabs being rotatable with respect to the shell;
      the sleeve has a clearance between the sleeve and the shell to allow angular tilting of the sleeve within the shell; and
      the sensor assembly is mounted in the first arm, with the tabs slidably seated in the grooves of the first pair of rails.

* * * * *

UNITED STATES PATENT AND TRADEMARK OFFICE
CERTIFICATE OF CORRECTION

| | |
|---|---|
| PATENT NO. | : 12,079,034 B2 |
| APPLICATION NO. | : 18/583641 |
| DATED | : September 3, 2024 |
| INVENTOR(S) | : Jan Zwierstra et al. |

It is certified that error appears in the above-identified patent and that said Letters Patent is hereby corrected as shown below:

On the Title Page

Item (72) Inventors: Line 5, after (US) please insert --Peter Szucs, Los Angeles, CA (US)--

Signed and Sealed this
Nineteenth Day of November, 2024

*Katherine Kelly Vidal*

Katherine Kelly Vidal
*Director of the United States Patent and Trademark Office*